(12) United States Patent
Buysse et al.

(10) Patent No.: US 7,828,798 B2
(45) Date of Patent: *Nov. 9, 2010

(54) LAPAROSCOPIC BIPOLAR ELECTROSURGICAL INSTRUMENT

(75) Inventors: Steven P. Buysse, Longmont, CO (US); Kate R. Lawes, Austin, TX (US); Dale F. Schmaltz, Fort Collins, CO (US); Michael J. Lands, Louisville, CO (US); S. Wade Lukianow, Boulder, CO (US); Kristin D. Johnson, Louisville, CO (US); Gary M. Couture, Longmont, CO (US); Lap P. Nguyen, Longmont, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 162 days.

This patent is subject to a terminal disclaimer.

(21) Appl. No.: 12/056,488

(22) Filed: Mar. 27, 2008

(65) Prior Publication Data

US 2008/0215051 A1 Sep. 4, 2008

Related U.S. Application Data

(63) Continuation of application No. 11/122,346, filed on May 5, 2005, now Pat. No. 7,377,920, which is a continuation of application No. 10/164,654, filed on Jun. 6, 2002, now abandoned, which is a continuation-in-part of application No. 09/591,330, filed on Jun. 9, 2000, now Pat. No. 6,451,018, which is a continuation of application No. 08/970,472, filed on Nov. 14, 1997, now Pat. No. 6,228,083.

(51) Int. Cl.
*A61B 18/14* (2006.01)

(52) U.S. Cl. .............................. 606/46; 606/48; 606/50; 606/51; 606/207; 606/208

(58) Field of Classification Search .................... 606/46, 606/48–52, 170, 207, 208
See application file for complete search history.

(56) References Cited

U.S. PATENT DOCUMENTS

| 371,664 A | 10/1887 | Brannan et al. |
|---|---|---|
| 702,472 A | 6/1902 | Pignolet |

(Continued)

FOREIGN PATENT DOCUMENTS

| CA | 2104423 | 2/1994 |
|---|---|---|

(Continued)

OTHER PUBLICATIONS

Sigel et al. "The Mechanism of Blood Vessel Closure by High Frequency Electrocoagulation" Surgery Gynecology & Obstetrics, Oct. 1965 pp. 823-831.

(Continued)

*Primary Examiner*—Lee S Cohen

(57) ABSTRACT

A laparoscopic bipolar electrosurgical instrument for sealing tissue includes a handle having an elongated tube affixed thereto. The tube includes first and second jaw members having electrically conductive sealing surfaces attached to a distal end thereof which are movable from a first position for approximating tissue to a second position for grasping tissue therebetween. The handle includes a fixed handle and a handle which is movable relative to the fixed handle to effect movement of the jaw members from the first position to the second position for grasping tissue. The jaw members connect to a source of electrosurgical energy such that the opposable sealing surfaces are capable of conducting electrosurgical energy through tissue held therebetween. A stop is included for maintaining a minimum separation distance between opposing sealing surfaces. A ratchet is also included to maintain a closure force in the range of about 7 kg/cm$^2$ to about 13 kg/cm$^2$ between opposing sealing surfaces.

7 Claims, 5 Drawing Sheets

U.S. PATENT DOCUMENTS

| | | |
|---|---|---|
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,305,156 A | 4/1941 | Grubel |
| 2,279,753 A | 4/1942 | Knopp |
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 3,073,311 A | 1/1963 | Tibbs et al. |
| 3,372,288 A | 3/1968 | Wigington |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Kamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| 5,334,183 A | 8/1994 | Wuchinich |

| | | | | | |
|---|---|---|---|---|---|
| 5,334,215 A | 8/1994 | Chen | 5,531,744 A | 7/1996 | Nardella et al. |
| 5,336,220 A | 8/1994 | Ryan et al. | 5,536,251 A | 7/1996 | Evard et al. |
| 5,336,221 A | 8/1994 | Anderson | 5,540,684 A | 7/1996 | Hassler, Jr. |
| 5,342,359 A | 8/1994 | Rydell | 5,540,685 A | 7/1996 | Parins et al. |
| 5,342,381 A | 8/1994 | Tidemand | 5,540,706 A | 7/1996 | Aust et al. |
| 5,342,393 A | 8/1994 | Stack | 5,540,715 A | 7/1996 | Katsaros et al. |
| 5,344,424 A | 9/1994 | Roberts et al. | 5,542,945 A | 8/1996 | Fritzsch |
| 5,350,391 A | 9/1994 | Iacovelli | 5,558,671 A | 9/1996 | Yates |
| 5,352,222 A | 10/1994 | Rydell | 5,558,672 A | 9/1996 | Edwards et al. |
| 5,354,271 A | 10/1994 | Voda | 5,562,619 A | 10/1996 | Mirarchi et al. |
| 5,356,408 A | 10/1994 | Rydell | 5,562,699 A | 10/1996 | Heimberger et al. |
| 5,366,477 A | 11/1994 | LeMarie, III et al. | 5,562,720 A | 10/1996 | Stern et al. |
| 5,368,600 A | 11/1994 | Failla et al. | 5,564,615 A | 10/1996 | Bishop et al. |
| 5,374,277 A | 12/1994 | Hassler | 5,569,241 A | 10/1996 | Edwardds |
| 5,376,089 A | 12/1994 | Smith | 5,569,243 A | 10/1996 | Kortenbach et al. |
| 5,383,875 A | 1/1995 | Bays et al. | 5,571,100 A | 11/1996 | Goble et al. |
| 5,383,897 A | 1/1995 | Wholey | 5,573,424 A | 11/1996 | Poppe |
| 5,389,098 A | 2/1995 | Tsuruta et al. | 5,573,534 A | 11/1996 | Stone |
| 5,389,103 A | 2/1995 | Melzer et al. | 5,573,535 A | 11/1996 | Viklund |
| 5,389,104 A | 2/1995 | Hahnen et al. | 5,575,799 A | 11/1996 | Bolanos et al. |
| 5,391,166 A | 2/1995 | Eggers | 5,575,805 A | 11/1996 | Li |
| 5,391,183 A | 2/1995 | Janzen et al. | 5,578,052 A | 11/1996 | Koros et al. |
| 5,396,900 A | 3/1995 | Slater et al. | 5,579,781 A | 12/1996 | Cooke |
| 5,403,312 A | 4/1995 | Yates et al. | 5,582,611 A | 12/1996 | Tsukagoshi et al. |
| 5,403,342 A | 4/1995 | Tovey et al. | 5,582,617 A | 12/1996 | Klieman et al. |
| 5,405,344 A | 4/1995 | Williamson et al. | 5,585,896 A | 12/1996 | Yamazaki et al. |
| 5,409,763 A | 4/1995 | Serizawa et al. | 5,590,570 A | 1/1997 | LeMaire, III et al. |
| 5,411,519 A | 5/1995 | Tovey et al. | 5,591,181 A | 1/1997 | Stone et al. |
| 5,411,520 A | 5/1995 | Nash et al. | 5,597,107 A | 1/1997 | Knodel et al. |
| 5,413,571 A | 5/1995 | Katsaros et al. | 5,601,224 A | 2/1997 | Bishop et al. |
| 5,415,656 A | 5/1995 | Tihon et al. | 5,601,601 A | 2/1997 | Tal et al. |
| 5,415,657 A | 5/1995 | Taymor-Luria | 5,601,641 A | 2/1997 | Stephens |
| 5,422,567 A | 6/1995 | Matsunaga | 5,603,711 A | 2/1997 | Parins et al. |
| 5,423,810 A | 6/1995 | Goble et al. | 5,603,723 A | 2/1997 | Aranyi et al. |
| 5,425,690 A | 6/1995 | Chang | 5,611,798 A | 3/1997 | Eggers |
| 5,425,739 A | 6/1995 | Jessen | 5,611,808 A | 3/1997 | Hossain et al. |
| 5,429,616 A | 7/1995 | Schaffer | 5,611,813 A | 3/1997 | Lichtman |
| 5,431,672 A | 7/1995 | Cote et al. | 5,620,415 A | 4/1997 | Lucey et al. |
| 5,431,674 A | 7/1995 | Basile et al. | 5,620,453 A | 4/1997 | Nallakrishnan |
| 5,437,292 A | 8/1995 | Kipshidze et al. | 5,620,459 A | 4/1997 | Lichtman |
| 5,438,302 A | 8/1995 | Goble | 5,624,452 A | 4/1997 | Yates |
| 5,439,478 A | 8/1995 | Palmer | 5,626,578 A | 5/1997 | Tihon |
| 5,441,517 A | 8/1995 | Kensey et al. | 5,626,609 A | 5/1997 | Zvenyatsky et al. |
| 5,443,463 A | 8/1995 | Stern et al. | 5,630,833 A | 5/1997 | Katsaros et al. |
| 5,443,464 A | 8/1995 | Russell et al. | 5,637,110 A | 6/1997 | Pennybacker et al. |
| 5,443,480 A | 8/1995 | Jacobs et al. | 5,638,003 A | 6/1997 | Hall |
| 5,445,638 A | 8/1995 | Rydell et al. | 5,643,294 A | 7/1997 | Tovey et al. |
| 5,445,658 A | 8/1995 | Durrfeld et al. | 5,647,869 A | 7/1997 | Goble et al. |
| 5,449,480 A | 9/1995 | Kuriya et al. | 5,647,871 A | 7/1997 | Levine et al. |
| 5,451,224 A | 9/1995 | Goble et al. | 5,649,959 A | 7/1997 | Hannam et al. |
| 5,454,823 A | 10/1995 | Richardson et al. | 5,655,650 A | 8/1997 | Naitou |
| 5,454,827 A | 10/1995 | Aust et al. | 5,658,281 A | 8/1997 | Heard |
| 5,456,684 A | 10/1995 | Schmidt et al. | D384,413 S | 9/1997 | Zlock et al. |
| 5,458,598 A | 10/1995 | Feinberg et al. | 5,662,667 A | 9/1997 | Knodel |
| 5,460,629 A | 10/1995 | Shlain et al. | 5,665,100 A | 9/1997 | Yoon |
| 5,461,765 A | 10/1995 | Linden et al. | 5,667,526 A | 9/1997 | Levin |
| 5,462,546 A | 10/1995 | Rydell | 5,674,220 A | 10/1997 | Fox et al. |
| 5,472,442 A | 12/1995 | Klicek | 5,674,229 A | 10/1997 | Tovey et al. |
| 5,472,443 A | 12/1995 | Cordis et al. | 5,681,282 A | 10/1997 | Eggers et al. |
| 5,478,351 A | 12/1995 | Meade et al. | 5,688,270 A | 11/1997 | Yates et al. |
| 5,480,406 A | 1/1996 | Nolan et al. | 5,690,652 A | 11/1997 | Wurster et al. |
| 5,480,409 A | 1/1996 | Riza | 5,690,653 A | 11/1997 | Richardson et al. |
| 5,484,436 A | 1/1996 | Eggers et al. | 5,693,051 A | 12/1997 | Schulze et al. |
| 5,496,312 A | 3/1996 | Klicek | 5,693,920 A | 12/1997 | Maeda |
| 5,496,317 A | 3/1996 | Goble et al. | 5,695,522 A | 12/1997 | LeMaire, III et al. |
| 5,496,347 A | 3/1996 | Hashiguchi et al. | 5,700,261 A | 12/1997 | Brinkerhoff |
| 5,499,997 A | 3/1996 | Sharpe et al. | 5,700,270 A | 12/1997 | Peyser et al. |
| 5,509,922 A | 4/1996 | Aranyi et al. | 5,702,390 A | 12/1997 | Austin et al. |
| 5,512,721 A | 4/1996 | Young et al. | 5,707,369 A | 1/1998 | Vaitekunas et al. |
| 5,514,134 A | 5/1996 | Rydell et al. | 5,709,680 A | 1/1998 | Yates et al. |
| 5,527,313 A | 6/1996 | Scott et al. | 5,716,366 A | 2/1998 | Yates |
| 5,528,833 A | 6/1996 | Sakuma | 5,720,744 A | 2/1998 | Eggleston et al. |
| 5,529,067 A | 6/1996 | Larsen et al. | 5,722,421 A | 3/1998 | Francese et al. |

| | | | | | |
|---|---|---|---|---|---|
| 5,725,536 A | 3/1998 | Oberlin et al. | 5,951,546 A | 9/1999 | Lorentzen |
| 5,727,428 A | 3/1998 | LeMaire, III et al. | 5,951,549 A | 9/1999 | Richardson et al. |
| 5,735,848 A | 4/1998 | Yates et al. | 5,954,720 A | 9/1999 | Wilson et al. |
| 5,743,906 A | 4/1998 | Parins et al. | 5,954,731 A | 9/1999 | Yoon |
| 5,752,973 A | 5/1998 | Kieturakis | 5,954,733 A | 9/1999 | Yoon |
| 5,755,717 A | 5/1998 | Yates et al. | 5,957,923 A | 9/1999 | Hahnen et al. |
| 5,759,188 A | 6/1998 | Yoon | 5,957,937 A | 9/1999 | Yoon |
| 5,766,130 A | 6/1998 | Selmonosky | 5,960,544 A | 10/1999 | Beyers |
| 5,766,166 A | 6/1998 | Hooven | 5,961,514 A | 10/1999 | Long et al. |
| 5,766,170 A | 6/1998 | Eggers | 5,964,758 A | 10/1999 | Dresden |
| 5,766,196 A | 6/1998 | Griffiths | 5,976,132 A | 11/1999 | Morris |
| 5,769,849 A | 6/1998 | Eggers | 5,984,932 A | 11/1999 | Yoon |
| 5,772,655 A | 6/1998 | Bauer et al. | 5,984,938 A | 11/1999 | Yoon |
| 5,772,670 A | 6/1998 | Brosa | 5,984,939 A | 11/1999 | Yoon |
| 5,776,128 A | 7/1998 | Eggers | 5,989,277 A | 11/1999 | LeMaire, III et al. |
| 5,776,130 A | 7/1998 | Buysse et al. | 5,993,466 A | 11/1999 | Yoon |
| 5,779,646 A | 7/1998 | Koblish et al. | 5,993,467 A | 11/1999 | Yoon |
| 5,779,701 A | 7/1998 | McBrayer et al. | 5,997,565 A | 12/1999 | Inoue |
| H1745 H | 8/1998 | Paraschac | 6,004,332 A | 12/1999 | Yoon et al. |
| 5,792,137 A | 8/1998 | Carr et al. | 6,004,335 A | 12/1999 | Vaitekunas et al. |
| 5,792,165 A | 8/1998 | Klieman et al. | 6,010,516 A | 1/2000 | Hulka et al. |
| 5,792,177 A | 8/1998 | Kaseda | 6,017,358 A | 1/2000 | Yoon et al. |
| 5,797,537 A | 8/1998 | Oberlin et al. | 6,021,693 A | 2/2000 | Feng-Sing |
| 5,797,927 A | 8/1998 | Yoon | 6,024,741 A | 2/2000 | Williamson et al. |
| 5,797,938 A | 8/1998 | Paraschac et al. | 6,024,743 A | 2/2000 | Edwards |
| 5,797,941 A | 8/1998 | Schulze et al. | 6,024,744 A | 2/2000 | Kese et al. |
| 5,797,958 A | 8/1998 | Yoon | 6,027,522 A | 2/2000 | Palmer |
| 5,800,449 A | 9/1998 | Wales | 6,030,384 A | 2/2000 | Nezhat |
| 5,807,393 A | 9/1998 | Williamson, IV et al. | 6,033,399 A | 3/2000 | Gines |
| 5,810,764 A | 9/1998 | Eggers et al. | 6,039,733 A | 3/2000 | Buysse et al. |
| 5,810,805 A | 9/1998 | Sutcu et al. | 6,041,679 A | 3/2000 | Slater et al. |
| 5,810,808 A | 9/1998 | Eggers | 6,050,996 A | 4/2000 | Schmaltz et al. |
| 5,810,811 A | 9/1998 | Yates et al. | 6,053,914 A | 4/2000 | Eggers et al. |
| 5,810,877 A | 9/1998 | Roth et al. | 6,053,933 A | 4/2000 | Balazs et al. |
| 5,814,043 A | 9/1998 | Shapeton | D424,694 S | 5/2000 | Tetzlaff et al. |
| 5,814,054 A | 9/1998 | Kortenbach et al. | D425,201 S | 5/2000 | Tetzlaff et al. |
| 5,817,093 A | 10/1998 | Williamson, IV et al. | 6,059,782 A | 5/2000 | Novak et al. |
| 5,817,119 A | 10/1998 | Klieman et al. | 6,066,139 A | 5/2000 | Ryan et al. |
| 5,820,630 A | 10/1998 | Lind | 6,074,386 A | 6/2000 | Goble et al. |
| 5,824,978 A | 10/1998 | Karasik et al. | 6,077,287 A | 6/2000 | Taylor et al. |
| 5,827,271 A | 10/1998 | Buysse et al. | 6,080,180 A | 6/2000 | Yoon et al. |
| 5,827,279 A | 10/1998 | Hughett et al. | RE36,795 E | 7/2000 | Rydell |
| 5,827,281 A | 10/1998 | Levin | 6,083,223 A | 7/2000 | Baker |
| 5,827,323 A | 10/1998 | Klieman et al. | 6,086,586 A | 7/2000 | Hooven |
| 5,827,548 A | 10/1998 | Lavallee et al. | 6,086,601 A | 7/2000 | Yoon |
| 5,833,690 A | 11/1998 | Yates et al. | 6,090,107 A | 7/2000 | Borgmeier et al. |
| 5,843,080 A | 12/1998 | Fleenor et al. | 6,096,037 A | 8/2000 | Mulier et al. |
| 5,849,022 A | 12/1998 | Sakashita et al. | 6,099,550 A | 8/2000 | Yoon |
| 5,853,412 A | 12/1998 | Mayenberger | 6,102,909 A | 8/2000 | Chen et al. |
| 5,859,527 A | 1/1999 | Cook | 6,106,542 A | 8/2000 | Toybin et al. |
| 5,860,976 A | 1/1999 | Billings et al. | 6,110,171 A | 8/2000 | Rydell |
| 5,876,401 A | 3/1999 | Schulze et al. | 6,113,596 A | 9/2000 | Hooven et al. |
| 5,876,412 A | 3/1999 | Piraka | 6,113,598 A | 9/2000 | Baker |
| 5,882,567 A | 3/1999 | Cavallaro et al. | 6,117,158 A | 9/2000 | Measamer et al. |
| 5,891,141 A | 4/1999 | Rydell | 6,122,549 A | 9/2000 | Sharkey et al. |
| 5,891,142 A | 4/1999 | Eggers et al. | 6,123,701 A | 9/2000 | Nezhat |
| 5,893,863 A | 4/1999 | Yoon | H1904 H | 10/2000 | Yates et al. |
| 5,893,875 A | 4/1999 | O'Connor et al. | 6,126,658 A | 10/2000 | Baker |
| 5,893,877 A | 4/1999 | Gampp, Jr. et al. | 6,126,665 A | 10/2000 | Yoon |
| 5,897,563 A | 4/1999 | Yoon et al. | 6,139,563 A | 10/2000 | Cosgrove, III et al. |
| 5,902,301 A | 5/1999 | Olig | 6,143,005 A | 11/2000 | Yoon et al. |
| 5,906,630 A | 5/1999 | Anderhub et al. | 6,152,923 A | 11/2000 | Ryan |
| 5,908,420 A | 6/1999 | Parins et al. | 6,162,220 A | 12/2000 | Nezhat |
| 5,908,432 A | 6/1999 | Pan | 6,171,316 B1 | 1/2001 | Kovac et al. |
| 5,911,719 A | 6/1999 | Eggers | 6,174,309 B1 | 1/2001 | Wrublewski et al. |
| 5,913,874 A | 6/1999 | Berns et al. | 6,178,628 B1 | 1/2001 | Clemens et al. |
| 5,921,916 A | 7/1999 | Aeikens et al. | 6,179,834 B1 | 1/2001 | Buysse et al. |
| 5,921,984 A | 7/1999 | Sutcu et al. | 6,179,837 B1 | 1/2001 | Hooven |
| 5,925,043 A | 7/1999 | Kumar et al. | 6,183,467 B1 | 2/2001 | Shapeton et al. |
| 5,928,136 A | 7/1999 | Barry | 6,187,003 B1 | 2/2001 | Buysse et al. |
| 5,935,126 A | 8/1999 | Riza | 6,190,386 B1 | 2/2001 | Rydell |
| 5,941,869 A | 8/1999 | Patterson et al. | 6,190,400 B1 | 2/2001 | Vandemoer et al. |
| 5,944,718 A | 8/1999 | Austin et al. | 6,193,718 B1 | 2/2001 | Kortenbach et al. |

| | | | | | | |
|---|---|---|---|---|---|---|
| 6,206,876 B1 | 3/2001 | Levine et al. | | 6,545,239 B2 | 4/2003 | Spedale et al. |
| 6,206,877 B1 | 3/2001 | Kese et al. | | 6,558,385 B1 | 5/2003 | McClurken et al. |
| 6,206,893 B1 | 3/2001 | Klein et al. | | 6,562,037 B2 | 5/2003 | Paton et al. |
| 6,214,028 B1 | 4/2001 | Yoon et al. | | 6,569,105 B1 | 5/2003 | Kortenbach et al. |
| 6,217,602 B1 | 4/2001 | Redmon | | 6,582,450 B2 | 6/2003 | Ouchi |
| 6,217,615 B1 | 4/2001 | Sioshansi et al. | | 6,585,735 B1 | 7/2003 | Frazier et al. |
| 6,221,039 B1 | 4/2001 | Durgin et al. | | 6,602,252 B2 | 8/2003 | Mollenauer |
| 6,223,100 B1 | 4/2001 | Green | | 6,605,790 B2 | 8/2003 | Yoshida |
| 6,224,593 B1 | 5/2001 | Ryan et al. | | 6,616,658 B2 | 9/2003 | Ineson |
| 6,224,614 B1 | 5/2001 | Yoon | | 6,616,661 B2 | 9/2003 | Wellman et al. |
| 6,228,080 B1 | 5/2001 | Gines | | 6,620,161 B2 | 9/2003 | Schulze et al. |
| 6,228,083 B1 | 5/2001 | Lands et al. | | 6,620,184 B2 | 9/2003 | De Laforcade et al. |
| 6,248,124 B1 | 6/2001 | Pedros et al. | | 6,626,901 B1 | 9/2003 | Treat et al. |
| 6,248,944 B1 | 6/2001 | Ito | | 6,638,287 B2 | 10/2003 | Danitz et al. |
| 6,261,307 B1 | 7/2001 | Yoon et al. | | 6,641,595 B1 | 11/2003 | Moran et al. |
| 6,267,761 B1 | 7/2001 | Ryan | | 6,652,514 B2 | 11/2003 | Ellman et al. |
| 6,270,497 B1 | 8/2001 | Sekino et al. | | 6,652,521 B2 | 11/2003 | Schulze |
| 6,270,508 B1 | 8/2001 | Klieman et al. | | 6,656,175 B2 | 12/2003 | Francischelli et al. |
| 6,273,887 B1 | 8/2001 | Yamauchi et al. | | 6,656,177 B2 | 12/2003 | Truckai et al. |
| 6,277,117 B1 | 8/2001 | Tetzlaff et al. | | 6,660,072 B2 | 12/2003 | Chatterjee |
| 6,280,458 B1 | 8/2001 | Boche et al. | | 6,663,639 B1 | 12/2003 | Laufer et al. |
| 6,283,961 B1 | 9/2001 | Underwood et al. | | 6,663,641 B1 | 12/2003 | Kovac et al. |
| D449,886 S | 10/2001 | Tetzlaff et al. | | 6,666,854 B1 | 12/2003 | Lange |
| 6,298,550 B1 | 10/2001 | Kirwan | | 6,669,696 B2 | 12/2003 | Bacher et al. |
| 6,302,424 B1 | 10/2001 | Gisinger et al. | | 6,673,092 B1 | 1/2004 | Bacher |
| 6,319,262 B1 | 11/2001 | Bates et al. | | 6,676,660 B2 | 1/2004 | Wampler et al. |
| 6,319,451 B1 | 11/2001 | Brune | | 6,676,676 B2 | 1/2004 | Danitz et al. |
| 6,322,561 B1 | 11/2001 | Eggers et al. | | 6,679,882 B1 | 1/2004 | Kornerup |
| 6,322,580 B1 | 11/2001 | Kanner | | 6,682,527 B2 | 1/2004 | Strul |
| 6,325,795 B1 | 12/2001 | Lindemann et al. | | 6,682,528 B2 | 1/2004 | Frazier et al. |
| 6,334,860 B1 | 1/2002 | Dorn | | 6,685,724 B1 | 2/2004 | Haluck |
| 6,334,861 B1 | 1/2002 | Chandler et al. | | 6,689,131 B2 | 2/2004 | McClurken |
| 6,345,532 B1 | 2/2002 | Coudray et al. | | 6,692,445 B2 | 2/2004 | Roberts et al. |
| 6,350,264 B1 | 2/2002 | Hooven | | 6,693,246 B1 | 2/2004 | Rudolph et al. |
| 6,352,536 B1 | 3/2002 | Buysse et al. | | 6,695,840 B2 | 2/2004 | Schulze |
| 6,358,249 B1 | 3/2002 | Chen et al. | | 6,702,810 B2 | 3/2004 | McClurken et al. |
| 6,358,259 B1 | 3/2002 | Swain et al. | | 6,723,092 B2 | 4/2004 | Brown et al. |
| 6,358,268 B1 | 3/2002 | Hunt et al. | | 6,726,068 B2 | 4/2004 | Miller |
| 6,364,879 B1 | 4/2002 | Chen et al. | | 6,726,686 B2 | 4/2004 | Buysse et al. |
| D457,958 S | 5/2002 | Dycus et al. | | 6,726,694 B2 | 4/2004 | Blatter et al. |
| D457,959 S | 5/2002 | Tetzlaff et al. | | 6,733,498 B2 | 5/2004 | Paton et al. |
| 6,387,094 B1 | 5/2002 | Eitenmuller | | 6,736,813 B2 | 5/2004 | Yamauchi et al. |
| 6,391,035 B1 | 5/2002 | Appleby et al. | | 6,743,229 B2 | 6/2004 | Buysse et al. |
| 6,398,779 B1 | 6/2002 | Buysse et al. | | 6,743,230 B2 | 6/2004 | Lutze et al. |
| 6,402,747 B1 | 6/2002 | Lindemann et al. | | 6,743,239 B1 | 6/2004 | Kuehn et al. |
| 6,409,728 B1 | 6/2002 | Ehr et al. | | 6,743,240 B2 | 6/2004 | Smith et al. |
| H2037 H | 7/2002 | Yates et al. | | 6,755,843 B2 | 6/2004 | Chung et al. |
| 6,419,675 B1 | 7/2002 | Gallo, Sr. | | 6,756,553 B1 | 6/2004 | Yamaguchi et al. |
| 6,425,896 B1 | 7/2002 | Baltschun et al. | | 6,757,977 B2 | 7/2004 | Dambal et al. |
| 6,432,112 B2 | 8/2002 | Brock et al. | | D493,888 S | 8/2004 | Reschke |
| 6,440,144 B1 | 8/2002 | Bacher | | 6,770,072 B2 | 8/2004 | Truckai et al. |
| 6,443,952 B1 | 9/2002 | Mulier et al. | | 6,773,409 B2 | 8/2004 | Truckai et al. |
| 6,443,970 B1 | 9/2002 | Schulze et al. | | 6,773,432 B1 | 8/2004 | Clayman et al. |
| 6,451,018 B1 | 9/2002 | Lands et al. | | 6,773,434 B2 | 8/2004 | Ciarrocca |
| 6,458,125 B1 | 10/2002 | Cosmescu | | 6,773,441 B1 | 8/2004 | Laufer et al. |
| 6,458,128 B1 | 10/2002 | Schulze | | 6,775,575 B2 | 8/2004 | Bommannan et al. |
| 6,458,130 B1 | 10/2002 | Frazier et al. | | 6,776,780 B2 | 8/2004 | Mulier et al. |
| 6,461,352 B2 | 10/2002 | Morgan et al. | | 6,786,905 B2 | 9/2004 | Swanson et al. |
| 6,461,368 B2 | 10/2002 | Fogarty et al. | | 6,790,217 B2 | 9/2004 | Schulze et al. |
| 6,464,701 B1 | 10/2002 | Hooven et al. | | 6,796,981 B2 | 9/2004 | Wham et al. |
| 6,464,702 B2 | 10/2002 | Schulze et al. | | D496,997 S | 10/2004 | Dycus et al. |
| 6,464,704 B2 | 10/2002 | Schmaltz et al. | | 6,800,825 B1 | 10/2004 | Sasaki et al. |
| 6,485,489 B2 | 11/2002 | Teirstein et al. | | 6,802,843 B2 | 10/2004 | Truckai et al. |
| 6,494,888 B1 | 12/2002 | Laufer et al. | | 6,808,525 B2 | 10/2004 | Latterell et al. |
| 6,500,176 B1 | 12/2002 | Truckai et al. | | D499,181 S | 11/2004 | Dycus et al. |
| 6,506,196 B1 | 1/2003 | Laufer | | 6,818,000 B2 | 11/2004 | Muller et al. |
| 6,508,815 B1 | 1/2003 | Strul et al. | | 6,821,285 B2 | 11/2004 | Laufer et al. |
| 6,511,480 B1 | 1/2003 | Tetzlaff et al. | | 6,835,200 B2 | 12/2004 | Laufer et al. |
| 6,514,215 B1 | 2/2003 | Ouchi | | 6,857,357 B2 | 2/2005 | Fujii |
| 6,514,252 B2 | 2/2003 | Nezhat et al. | | 6,860,880 B2 | 3/2005 | Treat et al. |
| 6,517,539 B1 | 2/2003 | Smith et al. | | 6,887,240 B1 | 5/2005 | Lands et al. |
| 6,527,771 B1 | 3/2003 | Weadock et al. | | 6,889,116 B2 | 5/2005 | Jinno |
| 6,533,784 B2 | 3/2003 | Truckai et al. | | 6,914,201 B2 | 7/2005 | Van Vooren et al. |

| | | | | | | |
|---|---|---|---|---|---|---|
| 6,926,716 | B2 | 8/2005 | Baker et al. | 7,223,264 | B2 | 5/2007 | Daniel et al. |
| 6,929,644 | B2 | 8/2005 | Truckai et al. | 7,223,265 | B2 | 5/2007 | Keppel |
| 6,932,810 | B2 | 8/2005 | Ryan | 7,232,440 | B2 | 6/2007 | Dumbauld et al. |
| 6,932,816 | B2 | 8/2005 | Phan | 7,241,288 | B2 | 7/2007 | Braun |
| 6,934,134 | B2 | 8/2005 | Mori et al. | 7,241,296 | B2 | 7/2007 | Buysse et al. |
| 6,936,061 | B2 | 8/2005 | Sasaki | 7,244,257 | B2 | 7/2007 | Podjahsky et al. |
| D509,297 | S | 9/2005 | Wells | 7,246,734 | B2 | 7/2007 | Shelto, IV |
| 6,942,662 | B2 | 9/2005 | Goble et al. | 7,248,944 | B2 | 7/2007 | Green |
| 6,943,311 | B2 | 9/2005 | Miyako | 7,252,667 | B2 | 8/2007 | Moses et al. |
| 6,953,430 | B2 | 10/2005 | Kodooka | 7,255,697 | B2 | 8/2007 | Dycus et al. |
| 6,953,461 | B2 | 10/2005 | McClurken et al. | 7,267,677 | B2 | 9/2007 | Johnson et al. |
| 6,958,070 | B2 | 10/2005 | Witt et al. | 7,270,660 | B2 | 9/2007 | Ryan |
| 6,960,210 | B2 | 11/2005 | Lands et al. | 7,270,664 | B2 | 9/2007 | Johnson et al. |
| 6,964,662 | B2 | 11/2005 | Kidooka | 7,276,068 | B2 | 10/2007 | Johnson et al. |
| 6,966,907 | B2 | 11/2005 | Goble | 7,300,435 | B2 | 11/2007 | Wham et al. |
| 6,972,017 | B2 | 12/2005 | Smith et al. | 7,303,557 | B2 | 12/2007 | Wham et al. |
| 6,977,495 | B2 | 12/2005 | Donofrio | 7,311,709 | B2 | 12/2007 | Truckai et al. |
| 6,979,786 | B2 | 12/2005 | Aukland et al. | 7,314,471 | B2 | 1/2008 | Holman |
| 6,981,628 | B2 | 1/2006 | Wales | 7,318,823 | B2 | 1/2008 | Sharps et al. |
| 6,987,244 | B2 | 1/2006 | Bauer | 7,329,256 | B2 | 2/2008 | Johnson et al. |
| 6,994,707 | B2 | 2/2006 | Ellman et al. | 7,329,257 | B2 | 2/2008 | Kanehira et al. |
| 6,994,709 | B2 | 2/2006 | Iida | D564,662 | S | 3/2008 | Moses et al. |
| 6,997,931 | B2 | 2/2006 | Sauer et al. | 7,338,526 | B2 | 3/2008 | Steinberg |
| 7,001,381 | B2 | 2/2006 | Harano et al. | 7,342,754 | B2 | 3/2008 | Fitzgerald et al. |
| 7,011,657 | B2 | 3/2006 | Truckai et al. | 7,344,268 | B2 | 3/2008 | Jhigamian |
| 7,033,354 | B2 | 4/2006 | Keppel | D567,943 | S | 4/2008 | Moses et al. |
| 7,033,356 | B2 | 4/2006 | Latterell et al. | 7,367,976 | B2 | 5/2008 | Lawes et al. |
| 7,041,102 | B2 | 5/2006 | Truckai et al. | 7,377,920 | B2 | 5/2008 | Buysse et al. |
| 7,044,948 | B2 | 5/2006 | Keppel | 7,384,420 | B2 | 6/2008 | Dycus et al. |
| 7,052,489 | B2 | 5/2006 | Griego et al. | 7,384,421 | B2 | 6/2008 | Hushka |
| 7,052,496 | B2 | 5/2006 | Yamauchi | 7,396,336 | B2 | 7/2008 | Orszulak et al. |
| 7,063,715 | B2 | 6/2006 | Onuki et al. | D575,395 | S | 8/2008 | Hushka |
| D525,361 | S | 7/2006 | Hushka | D575,401 | S | 8/2008 | Hixson et al. |
| 7,070,597 | B2 | 7/2006 | Truckai et al. | 7,435,249 | B2 | 10/2008 | Buysse et al. |
| 7,083,618 | B2 | 8/2006 | Couture et al. | 7,442,193 | B2 | 10/2008 | Shields et al. |
| 7,083,619 | B2 | 8/2006 | Truckai et al. | 7,442,194 | B2 | 10/2008 | Dumbauld et al. |
| 7,083,620 | B2 | 8/2006 | Jahns et al. | 7,445,621 | B2 | 11/2008 | Dumbauld et al. |
| 7,087,051 | B2 | 8/2006 | Bourne et al. | 7,458,972 | B2 | 12/2008 | Keppel |
| 7,087,054 | B2 | 8/2006 | Truckai et al. | 7,473,253 | B2 | 1/2009 | Dycus et al. |
| 7,090,673 | B2 | 8/2006 | Dycus et al. | 7,481,810 | B2 | 1/2009 | Dumbauld et al. |
| 7,090,689 | B2 | 8/2006 | Nagase et al. | 7,487,780 | B2 | 2/2009 | Hooven |
| 7,101,371 | B2 | 9/2006 | Dycus et al. | 7,491,201 | B2 | 2/2009 | Shields et al. |
| 7,101,372 | B2 | 9/2006 | Dycus et al. | 7,491,202 | B2 | 2/2009 | Odom et al. |
| 7,101,373 | B2 | 9/2006 | Dycus et al. | 7,500,975 | B2 | 3/2009 | Cunningham et al. |
| 7,103,947 | B2 | 9/2006 | Sartor et al. | 7,510,556 | B2 | 3/2009 | Nguyen et al. |
| 7,107,124 | B2 | 9/2006 | Green | 7,513,898 | B2 | 4/2009 | Johnson et al. |
| 7,112,199 | B2 | 9/2006 | Cosmescu | 7,540,872 | B2 | 6/2009 | Schechter et al. |
| D531,311 | S | 10/2006 | Guerra et al. | 7,549,995 | B2 | 6/2009 | Schultz |
| 7,115,123 | B2 | 10/2006 | Knowlton et al. | 7,553,312 | B2 | 6/2009 | Tetzlaff et al. |
| 7,118,570 | B2 | 10/2006 | Tetzlaff et al. | 2002/0013583 | A1 | 1/2002 | Camran et al. |
| 7,118,587 | B2 | 10/2006 | Dycus et al. | 2002/0049442 | A1 | 4/2002 | Roberts et al. |
| 7,131,860 | B2 | 11/2006 | Sartor et al. | 2002/0099372 | A1 | 7/2002 | Schulze et al. |
| 7,131,970 | B2 | 11/2006 | Moses et al. | 2002/0107517 | A1 | 8/2002 | Witt et al. |
| 7,131,971 | B2 | 11/2006 | Dycus et al. | 2002/0111624 | A1 | 8/2002 | Witt et al. |
| 7,135,020 | B2 | 11/2006 | Lawes et al. | 2002/0188294 | A1 | 12/2002 | Couture et al. |
| D533,942 | S | 12/2006 | Kerr et al. | 2003/0014052 | A1 | 1/2003 | Buysse et al. |
| 7,145,757 | B2 | 12/2006 | Shea et al. | 2003/0014053 | A1 | 1/2003 | Nguyen et al. |
| 7,147,638 | B2 | 12/2006 | Chapman et al. | 2003/0018331 | A1 | 1/2003 | Dycus et al. |
| 7,150,097 | B2 | 12/2006 | Sremcich et al. | 2003/0018332 | A1 | 1/2003 | Schmaltz et al. |
| 7,150,749 | B2 | 12/2006 | Dycus et al. | 2003/0032956 | A1 | 2/2003 | Lands et al. |
| 7,153,314 | B2 | 12/2006 | Laufer et al. | 2003/0069570 | A1 | 4/2003 | Witzel et al. |
| D535,027 | S | 1/2007 | James et al. | 2003/0069571 | A1 | 4/2003 | Treat et al. |
| 7,156,842 | B2 | 1/2007 | Sartor et al. | 2003/0078578 | A1 | 4/2003 | Truckai et al. |
| 7,156,846 | B2 | 1/2007 | Dycus et al. | 2003/0109875 | A1 | 6/2003 | Tetzlaff et al. |
| 7,160,298 | B2 | 1/2007 | Lawes et al. | 2003/0114851 | A1 | 6/2003 | Truckai et al. |
| 7,160,299 | B2 | 1/2007 | Baily | 2003/0139741 | A1 | 7/2003 | Goble et al. |
| 7,169,146 | B2 | 1/2007 | Truckai et al. | 2003/0139742 | A1 | 7/2003 | Wampler et al. |
| 7,179,255 | B2 | 2/2007 | Lettice et al. | 2003/0158548 | A1 | 8/2003 | Phan et al. |
| 7,179,258 | B2 | 2/2007 | Buysse et al | 2003/0158549 | A1 | 8/2003 | Swanson |
| 7,195,631 | B2 | 3/2007 | Dumbauld | 2003/0171747 | A1 | 9/2003 | Kanehira et al. |
| D541,418 | S | 4/2007 | Schechter et al. | 2003/0181910 | A1 | 9/2003 | Dycus et al. |
| 7,207,990 | B2 | 4/2007 | Lands et al. | 2003/0216732 | A1 | 11/2003 | Truckai et al. |
| D541,938 | S | 5/2007 | Kerr et al | 2003/0220637 | A1 | 11/2003 | Truckai et al. |

| | | | | | |
|---|---|---|---|---|---|
| 2003/0229344 A1 | 12/2003 | Dycus et al. | 2006/0264922 A1 | 11/2006 | Sartor et al. |
| 2003/0236325 A1 | 12/2003 | Bonora | 2006/0264931 A1 | 11/2006 | Chapman et al. |
| 2003/0236518 A1 | 12/2003 | Marchitto et al. | 2006/0283093 A1 | 12/2006 | Petrovic et al. |
| 2004/0030330 A1 | 2/2004 | Brassell et al. | 2006/0287641 A1 | 12/2006 | Perlin |
| 2004/0030332 A1 | 2/2004 | Knowlton et al. | 2007/0016182 A1 | 1/2007 | Lipson et al. |
| 2004/0049185 A1 | 3/2004 | Latterell et al. | 2007/0016187 A1 | 1/2007 | Weinberg et al. |
| 2004/0064151 A1 | 4/2004 | Mollenauer | 2007/0043352 A1 | 2/2007 | Garrison et al. |
| 2004/0073238 A1 | 4/2004 | Makower | 2007/0043353 A1 | 2/2007 | Dycus et al. |
| 2004/0073256 A1 | 4/2004 | Marchitto et al. | 2007/0060919 A1 | 3/2007 | Isaacson et al. |
| 2004/0078035 A1 | 4/2004 | Kanehira et al. | 2007/0062017 A1 | 3/2007 | Dycus et al. |
| 2004/0082952 A1 | 4/2004 | Dycus et al. | 2007/0074807 A1 | 4/2007 | Guerra |
| 2004/0087943 A1 | 5/2004 | Dycus et al. | 2007/0078456 A1 | 4/2007 | Dumbauld et al. |
| 2004/0115296 A1 | 6/2004 | Duffin | 2007/0078458 A1 | 4/2007 | Dumbauld et al. |
| 2004/0116924 A1 | 6/2004 | Dycus et al. | 2007/0078459 A1 | 4/2007 | Johnson et al. |
| 2004/0116979 A1 | 6/2004 | Truckai et al. | 2007/0088356 A1 | 4/2007 | Moses et al. |
| 2004/0122423 A1 | 6/2004 | Dycus et al. | 2007/0106295 A1 | 5/2007 | Garrison et al. |
| 2004/0143263 A1 | 7/2004 | Schechter et al. | 2007/0106297 A1 | 5/2007 | Dumbauld et al. |
| 2004/0148035 A1 | 7/2004 | Barrett et al. | 2007/0118111 A1 | 5/2007 | Weinberg |
| 2004/0162557 A1 | 8/2004 | Tetzlaff et al. | 2007/0118115 A1 | 5/2007 | Artale et al. |
| 2004/0193153 A1 | 9/2004 | Sarter et al. | 2007/0142833 A1 | 6/2007 | Dycus et al. |
| 2004/0199181 A1 | 10/2004 | Knodel et al. | 2007/0142834 A1 | 6/2007 | Dumbauld |
| 2004/0210282 A1 | 10/2004 | Flock et al. | 2007/0156139 A1 | 7/2007 | Schechter et al. |
| 2004/0224590 A1 | 11/2004 | Rawa et al. | 2007/0156140 A1 | 7/2007 | Baily |
| 2004/0230189 A1 | 11/2004 | Keppel | 2007/0173811 A1 | 7/2007 | Couture et al. |
| 2004/0236326 A1 | 11/2004 | Schulze et al. | 2007/0173814 A1 | 7/2007 | Hixson et al. |
| 2004/0243125 A1 | 12/2004 | Dycus et al. | 2007/0179499 A1 | 8/2007 | Garrison |
| 2004/0249371 A1 | 12/2004 | Dycus et al. | 2007/0198011 A1 | 8/2007 | Sugita |
| 2004/0249374 A1 | 12/2004 | Tetzlaff et al. | 2007/0203485 A1 | 8/2007 | Keppel |
| 2004/0260281 A1 | 12/2004 | Baxter, III et al. | 2007/0213706 A1 | 9/2007 | Dumbauld et al. |
| 2005/0004564 A1 | 1/2005 | Wham et al. | 2007/0213707 A1 | 9/2007 | Dumbauld et al. |
| 2005/0004569 A1 | 1/2005 | Witt et al. | 2007/0213708 A1 | 9/2007 | Dumbauld et al. |
| 2005/0021025 A1 | 1/2005 | Buysse et al. | 2007/0213712 A1 | 9/2007 | Buysse et al. |
| 2005/0021027 A1 | 1/2005 | Shields et al. | 2007/0255279 A1 | 11/2007 | Buysse et al. |
| 2005/0033278 A1 | 2/2005 | McClurken et al. | 2007/0260235 A1 | 11/2007 | Podhajsky |
| 2005/0059934 A1 | 3/2005 | Wenchell et al. | 2007/0260238 A1 | 11/2007 | Guerra |
| 2005/0096645 A1 | 5/2005 | Wellman et al. | 2007/0260241 A1 | 11/2007 | Dalla Betta et al. |
| 2005/0101951 A1 | 5/2005 | Wham et al. | 2007/0260242 A1 | 11/2007 | Dycus et al. |
| 2005/0101952 A1 | 5/2005 | Lands et al. | 2007/0265616 A1 | 11/2007 | Couture et al. |
| 2005/0113818 A1 | 5/2005 | Sartor et al. | 2008/0004616 A1 | 1/2008 | Patrick |
| 2005/0113819 A1 | 5/2005 | Wham et al. | 2008/0009860 A1 | 1/2008 | Odom |
| 2005/0113826 A1 | 5/2005 | Johnson et al. | 2008/0015575 A1 | 1/2008 | Odom et al. |
| 2005/0113828 A1 | 5/2005 | Shields et al. | 2008/0021450 A1 | 1/2008 | Couture |
| 2005/0137590 A1 | 6/2005 | Lawes et al. | 2008/0033428 A1 | 2/2008 | Artale et al. |
| 2005/0149017 A1 | 7/2005 | Dycus | 2008/0039835 A1 | 2/2008 | Johnson et al. |
| 2005/0149151 A1 | 7/2005 | Orszulak et al. | 2008/0039836 A1 | 2/2008 | Odom et al. |
| 2005/0154387 A1 | 7/2005 | Moses et al. | 2008/0045947 A1 | 2/2008 | Johnson et al. |
| 2005/0187547 A1 | 8/2005 | Sugi | 2008/0058802 A1 | 3/2008 | Couture et al. |
| 2005/0197659 A1 | 9/2005 | Bahney | 2008/0082100 A1 | 4/2008 | Orton et al. |
| 2005/0203504 A1 | 9/2005 | Wham et al. | 2008/0091189 A1 | 4/2008 | Carlton |
| 2005/0240179 A1 | 10/2005 | Buysse et al. | 2008/0114356 A1 | 5/2008 | Johnson et al. |
| 2006/0052778 A1 | 3/2006 | Chapman et al. | 2008/0167651 A1 | 7/2008 | Tetzlaff et al. |
| 2006/0052779 A1 | 3/2006 | Hammill | 2008/0195093 A1 | 8/2008 | Couture et al. |
| 2006/0064085 A1 | 3/2006 | Schechter et al. | 2008/0215051 A1 | 9/2008 | Buysse et al. |
| 2006/0064086 A1 | 3/2006 | Odom | 2008/0243120 A1 | 10/2008 | Lawes et al. |
| 2006/0074417 A1 | 4/2006 | Cunningham et al. | 2008/0249527 A1 | 10/2008 | Couture |
| 2006/0079888 A1 | 4/2006 | Mulier et al. | 2008/0312653 A1 | 12/2008 | Arts et al. |
| 2006/0079890 A1 | 4/2006 | Guerra | 2008/0319442 A1 | 12/2008 | Unger et al. |
| 2006/0079891 A1 | 4/2006 | Arts et al. | 2009/0012520 A1 | 1/2009 | Hixson et al. |
| 2006/0079933 A1 | 4/2006 | Hushka et al. | 2009/0018535 A1 | 1/2009 | Schechter et al. |
| 2006/0084973 A1 | 4/2006 | Hushka | 2009/0024126 A1 | 1/2009 | Artale et al. |
| 2006/0089670 A1 | 4/2006 | Hushka | 2009/0043304 A1 | 2/2009 | Tetzlaff et al. |
| 2006/0116675 A1 | 6/2006 | McClurken et al. | 2009/0048596 A1 | 2/2009 | Shields et al. |
| 2006/0129146 A1 | 6/2006 | Dycus et al. | 2009/0062794 A1 | 3/2009 | Buysse et al. |
| 2006/0167450 A1 | 7/2006 | Johnson et al. | 2009/0082766 A1 | 3/2009 | Unger et al. |
| 2006/0167452 A1 | 7/2006 | Moses et al. | 2009/0082767 A1 | 3/2009 | Unger et al. |
| 2006/0173452 A1 | 8/2006 | Buysse et al. | 2009/0082769 A1 | 3/2009 | Unger et al. |
| 2006/0189981 A1 | 8/2006 | Dycus et al. | 2009/0088738 A1 | 4/2009 | Guerra et al. |
| 2006/0190035 A1 | 8/2006 | Hushka et al. | 2009/0088739 A1 | 4/2009 | Hushka et al. |
| 2006/0217709 A1 | 9/2006 | Couture et al. | 2009/0088740 A1 | 4/2009 | Guerra et al. |
| 2006/0224158 A1 | 10/2006 | Odom et al. | 2009/0088741 A1 | 4/2009 | Hushka et al. |
| 2006/0229666 A1 | 10/2006 | Suzuki et al. | 2009/0088744 A1 | 4/2009 | Townsend |
| 2006/0253126 A1 | 11/2006 | Bjerken et al. | 2009/0088745 A1 | 4/2009 | Hushka et al. |
| 2006/0259036 A1 | 11/2006 | Tetzlaff et al. | 2009/0088746 A1 | 4/2009 | Hushka et al. |

| | | | | | | |
|---|---|---|---|---|---|---|
| 2009/0088747 | A1 | 4/2009 | Hushka et al. | EP | 1642543 | | 4/2006 |
| 2009/0088748 | A1 | 4/2009 | Guerra et al. | EP | 1645238 | A1 | 4/2006 |
| 2009/0088749 | A1 | 4/2009 | Hushka et al. | EP | 1645240 | A2 | 4/2006 |
| 2009/0088750 | A1 | 4/2009 | Hushka et al. | EP | 1649821 | | 4/2006 |
| 2009/0112206 | A1 | 4/2009 | Dumbauld et al. | EP | 1707143 | A1 | 10/2006 |
| 2009/0131934 | A1 | 5/2009 | Odom et al. | EP | 1769765 | | 4/2007 |
| 2009/0149853 | A1 | 6/2009 | Shields et al. | EP | 1769766 | | 4/2007 |
| 2009/0149854 | A1 | 6/2009 | Cunningham et al. | EP | 1929970 | | 6/2008 |
| 2009/0171350 | A1 | 7/2009 | Dycus et al. | EP | 1683496 | | 12/2008 |
| 2009/0171353 | A1 | 7/2009 | Johnson et al. | GB | 623316 | | 5/1949 |
| 2009/0182327 | A1 | 7/2009 | Unger | GB | 1490585 | | 11/1977 |
| 2009/0187188 | A1 | 7/2009 | Guerra et al. | GB | 2214430 | A | 6/1989 |

FOREIGN PATENT DOCUMENTS

| | | | |
|---|---|---|---|
| GB | 2213416 | A | 8/1989 |
| JP | 501068 | | 9/1984 |
| JP | 502328 | | 3/1992 |
| DE | 2415263 | | 10/1975 |
| DE | 2514501 | | 10/1976 |
| JP | 5-5106 | | 1/1993 |
| DE | 2627679 | | 1/1977 |
| JP | 5-40112 | | 2/1993 |
| DE | 3612646 | | 4/1987 |
| JP | 06343644 | A2 | 12/1994 |
| DE | 8712328 | | 3/1988 |
| JP | 07265328 | A2 | 10/1995 |
| DE | 4303882 | | 8/1994 |
| JP | 08056955 | A2 | 3/1996 |
| DE | 4403252 | | 8/1995 |
| JP | 08252263 | A2 | 10/1996 |
| DE | 19515914 | | 7/1996 |
| JP | 09010223 | A2 | 1/1997 |
| DE | 29616210 | | 1/1997 |
| JP | 11244298 | A2 | 9/1999 |
| DE | 19608716 | | 4/1997 |
| JP | 2000342599 | A2 | 12/2000 |
| DE | 19751106 | | 5/1998 |
| JP | 2000350732 | A2 | 12/2000 |
| DE | 19751108 | | 5/1999 |
| JP | 2001008944 | A2 | 1/2001 |
| DE | 19738457 | | 1/2009 |
| JP | 2001029356 | A2 | 2/2001 |
| EP | 0364216 | A1 | 4/1990 |
| JP | 2001128990 | A2 | 5/2001 |
| EP | 0467501 | | 1/1992 |
| SU | 401367 | | 11/1974 |
| EP | 518230 | A1 | 12/1992 |
| WO | WO 89/00757 | | 1/1989 |
| EP | 0541930 | B1 | 5/1993 |
| WO | WO 92/04873 | | 4/1992 |
| EP | 0572131 | | 12/1993 |
| WO | WO 92/06642 | | 4/1992 |
| EP | 584787 | A1 | 3/1994 |
| WO | WO 93/21845 | | 11/1993 |
| EP | 0589453 | A2 | 3/1994 |
| WO | WO 94/08524 | | 4/1994 |
| EP | 0589555 | | 3/1994 |
| WO | WO 94/20025 | | 9/1994 |
| EP | 0623316 | A1 | 11/1994 |
| WO | WO 95/02369 | | 1/1995 |
| EP | 0624348 | A2 | 11/1994 |
| WO | WO 95/07662 | | 3/1995 |
| EP | 0650701 | A1 | 5/1995 |
| WO | WO 95/15124 | | 6/1995 |
| EP | 0694290 | A3 | 3/1996 |
| WO | WO 96/05776 | | 2/1996 |
| EP | 0717966 | A1 | 6/1996 |
| WO | WO 96/22056 | | 7/1996 |
| EP | 0754437 | A3 | 3/1997 |
| WO | WO 96/13218 | | 9/1996 |
| EP | 0517243 | | 9/1997 |
| WO | WO 97/00646 | | 1/1997 |
| EP | 853922 | A1 | 7/1998 |
| WO | WO 97/00647 | | 1/1997 |
| EP | 0875209 | A1 | 11/1998 |
| WO | WO 97/10764 | | 3/1997 |
| EP | 0878169 | A1 | 11/1998 |
| WO | WO 97/24073 | | 7/1997 |
| EP | 0887046 | A3 | 1/1999 |
| WO | WO 97/24993 | | 7/1997 |
| EP | 0923907 | A1 | 6/1999 |
| WO | WO 98/27880 | | 7/1998 |
| EP | 0986990 | A1 | 3/2000 |
| WO | WO 99/03407 | | 1/1999 |
| EP | 1034747 | A1 | 9/2000 |
| WO | WO 99/03408 | | 1/1999 |
| EP | 1034748 | A1 | 9/2000 |
| WO | WO 99/03409 | | 1/1999 |
| EP | 1025807 | A3 | 10/2000 |
| WO | WO 99/12488 | | 3/1999 |
| EP | 1034746 | A3 | 10/2000 |
| WO | WO 99/23933 | | 5/1999 |
| EP | 1050278 | A1 | 11/2000 |
| WO | WO 99/40857 | | 8/1999 |
| EP | 1053719 | A1 | 11/2000 |
| WO | WO 99/40861 | | 8/1999 |
| EP | 1053720 | A1 | 11/2000 |
| WO | WO 99/51158 | | 10/1999 |
| EP | 1055399 | A1 | 11/2000 |
| WO | WO 99/66850 | | 12/1999 |
| EP | 1055400 | A1 | 11/2000 |
| WO | WO 00/24330 | | 5/2000 |
| EP | 1080694 | A1 | 3/2001 |
| WO | WO 00/24331 | | 5/2000 |
| EP | 1082944 | A1 | 3/2001 |
| WO | WO 00/36986 | | 6/2000 |
| EP | 1159926 | A2 | 12/2001 |
| WO | WO 00/41638 | | 7/2000 |
| EP | 1177771 | | 2/2002 |
| WO | WO 00/47124 | | 8/2000 |
| EP | 1301135 | A | 4/2003 |
| WO | WO 00/53112 | | 9/2000 |
| EP | 1330991 | A1 | 7/2003 |
| WO | WO 01/17448 | | 3/2001 |
| EP | 1486177 | A2 | 6/2004 |
| WO | WO 01/54604 | | 8/2001 |
| EP | 1472984 | A1 | 11/2004 |
| WO | WO 02/07627 | | 1/2002 |
| EP | 0774232 | | 1/2005 |
| WO | WO 02/067798 | | 9/2002 |
| EP | 1527747 | A2 | 5/2005 |
| WO | WO 02/080783 | | 10/2002 |
| EP | 1530952 | A1 | 5/2005 |
| WO | WO 02/080784 | | 10/2002 |
| EP | 1532932 | A1 | 5/2005 |
| WO | WO 02/080785 | | 10/2002 |
| EP | 1535581 | A2 | 6/2005 |
| WO | WO 02/080786 | | 10/2002 |
| EP | 1609430 | A1 | 12/2005 |
| WO | WO 02/080793 | | 10/2002 |
| EP | 1632192 | A1 | 3/2006 |
| WO | WO 02/080794 | | 10/2002 |
| | | | |
| | | | |
| WO | WO 02/080795 | | 10/2002 |

| | | |
|---|---|---|
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/061500 | 7/2003 |
| WO | WO 03/090630 | 11/2003 |
| WO | WO 03/101311 | 12/2003 |
| WO | WO 2004/032776 | 4/2004 |
| WO | WO 2004/032777 | 4/2004 |
| WO | WO 2004/052221 | 6/2004 |
| WO | WO 2004/073488 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 | 1/2005 |
| WO | WO 2005/004735 | 1/2005 |
| WO | WO 2005/110264 | 11/2005 |
| WO | WO 2008/045348 | 4/2008 |
| WO | WO 2008/045350 | 4/2008 |

OTHER PUBLICATIONS

Bergdahl et al. "Studies on Coagulation and the Development of an Automatic Computerized Bipolar Coagulator" J.Neurosurg, vol. 75, Jul. 1991, pp. 148-151.
Kennedy et al. "High-burst-strength, feedback-controlled bipolar vessel sealing" Surgical Endoscopy (1998) 12: 876-878.
Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Johnson et al. "Evaluation of the LigaSure Vessel Sealing System in Hemorrhoidectormy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001 pp. 21-24.
Heniford et al. "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.
McLellan et al. "Vessel Sealing for Hemostasis During Pelvic Surgery" Int'l Federation of Gynecology and Obstetrics FIGO World Congress 2000, Washington, D.C.
Levy et al. "Use of a New Energy-based Vessel Ligation Device During Vaginal Hysterectomy" Int'l Federation of Gynecology and Obstetrics (FIGO) World Congress 1999.
Crawford et al. "Use of the LigaSure Vessel Sealing System in Urologic Cancer Surger" Grand Rounds in Urology 1999 vol. 1 Issue 4 pp. 10-17.
Rothenberg et al. "Use of the LigaSure Vessel Sealing System in Minimally Invasive Surgery in Children" Int'l Pediatric Endosurgery Group (IPEG) 2000.
Palazzo et al. "Randomized clinical trial of Ligasure versus open haemorrhoidectomy" British Journal of Surgery 2002, 89, 154-157.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery Sales/Product Literature; Jan. 2004.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC 2003.
"Reducing Needlestick Injuries in the Operating Room" Sales/Product Literature 2001.

Chung et al., "Clinical Experience of Sutureless Closed Hemorrhoidectomy with LigaSure" Diseases of the Colon & Rectum vol. 46, No. 1 Jan. 2003.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Paul G. Horgan, "A Novel Technique for Parenchymal Division During Hepatectomy" The American Journal of Surgery, vol. 181, No. 3, Apr. 2001 pp. 236-237.
W. Scott Helton, "LigaSure Vessel Sealing System: Revolutionary Hemostasis Product for General Surgery" Sales/Product Literature 1999.
Michael Choti, "Abdominoperineal Resection with the LigaSure Vessel Sealing System and LigaSure Atlas 20 cm Open Instrument" Innovations That Work, Jun. 2003.
Craig Johnson, "Use of the LigaSure Vessel Sealing System in Bloodless Hemorrhoidectomy" Innovations That Work, Mar. 2000.
Muller et al., "Extended Left Hemicolectomy Using the LigaSure Vessel Sealing System" Innovations That Work, Sep. 1999.
Herman et al., "Laparoscopic Intestinal Resection With the LigaSure Vessel Sealing System: A Case Report" Innovations That Work, Feb. 2002.
Carus et al., "Initial Experience With The LigaSure Vessel Sealing System in Abdominal Surgery" Innovations That Work, Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
McLellan et al. "Vessel Sealing For Hemostasis During Gynecologic Surgery" Sales/Product Literature 1999.
Sengupta et al., "Use of a Computer-Controlled Bipolar Diathermy System in Radical Prostatectomies and Other Open Urological Surgery" ANZ Journal of Surgery (2001) 71.9 pp. 538-540.
Olsson et al. "Radical Cystectomy in Females" Current Surgical Techniques in Urology, vol. 14, Issue 3, 2001.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
E. David Crawford "Evaluation of a New Vessel Sealing Device in Urologic Cancer Surgery" Sales/Product Literature 2000.
Joseph Ortenberg "LigaSure System Used in Laparoscopic 1st and 2nd Stage Orchiopexy" Innovations That Work, Nov. 2002.
Koyle et al., "Laparoscopic Palomo Varicocele Ligation in Children and Adolescents" Pediatric Endosurgery & Innovative Techniques, vol. 6, No. 1, 2002.
Dulemba et al. "Use of a Bipolar Electrothermal Vessel Sealer in Laparoscopically Assisted Vaginal Hysterectomy" Sales/Product Literature; Jan. 2004.
Johnson et al. "Evaluation of a Bipolar Electrothermal Vessel Sealing Device in Hemorrhoidectomy" Sales/Product Literature; Jan. 2004.
Int'l Search Report PCT/US98/18640 dated Dec. 17, 1998.
Int'l Search Report PCT/US98/23950 dated Dec. 29, 1998.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report EP 98944778 dated Oct. 31, 2000.
Int'l Search Report EP 98958575.7 dated Sep. 20, 2002.
Int'l Search Report EP 04027314 dated Mar. 10, 2005.
Int'l Search Report EP 04027479 dated Mar. 8, 2005.
Int'l Search Report EP 04027705 dated Feb. 3, 2005.

Int'l Search Report EP 04013772 dated Apr. 1, 2005.
Int'l Search Report EP 05013463.4 dated Sep. 28, 2005.
Int'l Search Report EP 05013895 dated Oct. 14, 2005.
Int'l Search Report EP 05016399 dated Jan. 5, 2006.
Int'l Search Report EP 05017281 dated Nov. 16, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 06005185.1 dated Apr. 18, 2006.
Int'l Search Report EP 06006716 dated Aug. 4, 2006.
Int'l Search Report EP 06008779.8 dated Jun. 13, 2006.
Int'l Search Report EP 1683496 dated Jun. 13, 2006.
Int'l Search Report EP 06014461.5 dated Oct. 20, 2006.
Int'l Search Report EP 06020584.6 dated Jan. 12, 2007.
Int'l Search Report EP 06020583.8, dated Jan. 30, 2007.
Int'l Search Report EP 06020756.0 dated Feb. 5, 2007.
Int'l Search Report EP 06024123.9 dated Feb. 26. 2007.
Int'l Search Report EP 04 752343.6 dated Jul. 20, 2007.
Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report Extended—EP 07 009029.5 dated Jul. 12, 2007.
Int'l Search Report EP 07 009321.6 dated Aug. 17. 2007.
Int'l Search Report EP 06 020574.7 dated Sep. 21, 2007.
Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16. 2008.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Crouch et al. "A Velocity-Dependent Model for Needle Insertion in Soft Tissue" MICCAI 2005; LNCS 3750 pp. 624-632, Dated: 2005.
Int'l Search Report EP 98957771 dated Aug. 9, 2001.
Int'l Search Report EP 05002671.5 dated Dec. 22, 2008.
Int'l Search Report EP 05002674.9 dated Jan. 16, 2009.
Int'l Search Report EP 05019429.9 dated May 6, 2008.
Int'l Search Report EP 06008515.6 dated Jan. 8, 2009.
Int'l Search Report EP 07 014016 dated Jan. 28, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 Dated Jun. 15, 2009.
Int'l Search Report EP 09 152898.4 Dated Jun. 10, 2009.
Int'l Search Report PCT/US98/24281 dated Feb. 22, 1999.
Int'l Search Report PCT/US03/28534 dated Dec. 19, 2003.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

LAPAROSCOPIC BIPOLAR ELECTROSURGICAL INSTRUMENT

CROSS REFERENCE TO RELATED APPLICATIONS

This application is a continuation of U.S. patent application Ser. No. 11/122,346 (now U.S. Pat. No. 7,377,920) filed May 5, 2005, which is a continuation of U.S. patent application Ser. No. 10/164,654 filed Jun. 6, 2002, now abandoned, which is a continuation-in-part of U.S. application Ser. No. 09/591,330 filed on Jun. 9, 2000, now U.S. Pat. No. 6,451,018, which is a continuation of U.S. application Ser. No. 08/970,472 filed on Nov. 14, 1997, now U.S. Pat. No. 6,228,083, the entire contents of all of which being incorporated by reference herein.

BACKGROUND

1. Field of the Invention

This disclosure relates to an electrosurgical instrument for performing laparoscopic surgical procedures, and more particularly to a laparoscopic electrosurgical instrument that is capable of grasping vessels and vascular tissue with sufficient force between two bipolar jaws to seal the vessel or vascular tissue.

2. Background of Related Art

Laparoscopic surgical instruments are used to perform surgical operation without making large incisions in the patient. The laparoscopic instruments are inserted into the patient through a cannula, or port, that has been made with a trocar. Typical sizes for cannulas range from three millimeters to twelve millimeters. Smaller cannulas are usually preferred, and this presents a design challenge to instrument manufacturers who must find ways to make surgical instruments that fit through the cannulas.

Certain surgical procedures require cutting blood vessels or vascular tissue. This sometimes presents a problem for surgeons because it is difficult to suture blood vessels using laparoscopic tools. Very small blood vessels, in the range below two millimeters in diameter, can often be closed using standard electrosurgical techniques. If a larger vessel is severed, it may be necessary for the surgeon to convert the laparoscopic procedure into an open-surgical procedure and thereby abandon the benefits of laparoscopy.

Several journal articles have disclosed methods for sealing small blood vessels using electrosurgery. An article entitled Studies on Coagulation and the Development of an Automatic Computerized Bipolar Coagulator, J. Neurosurg., Volume 75, July 1991, describes a bipolar coagulator which is used to seal small blood vessels. The article states that it was not possible to safely coagulate arteries with a diameter larger than 2 to 2.5 mm. A second article is entitled Automatically Controlled Bipolar Electrocoagulation—"COA-COMP", Neurosurg. Rev. (1984), pp. 187-190. This article describes a method for terminating electrosurgical power to the vessel so that charring of the vessel walls can be avoided.

It has been recently determined that electrosurgical methods may be able to seal larger vessels using an appropriate electrosurgical power curve, coupled with an instrument capable of applying a large closure force to the vessel walls. It is thought that the process of coagulating small vessels is fundamentally different than electrosurgical vessel sealing. Coagulation is defined as a process of desiccating tissue wherein the tissue cells are ruptured and dried. Vessel sealing is defined as the process of liquefying the collagen in the tissue so that it cross-links and reforms into a fused mass. Thus, coagulation of small vessels is sufficient to permanently close them. Larger vessels need to be sealed to assure permanent closure.

It would be desirable to have a surgical tool capable of applying electrosurgical energy, capable of applying a large closure force to the vessel walls, and also capable of fitting through a cannula. A large closure force between the jaws typically requires a large moment about the pivot for each jaw. This presents a challenge because the first and second pins have a small moment arm with respect to the pivot of each jaw. A large force, coupled with a small moment arm, is undesirable because the large forces may shear the first and second pins. It is also undesirable to increase the moment arm of the first and second pins because the physical size of the yoke might not fit through a cannula.

Several bipolar laparoscopic instruments are known. For example, U.S. Pat. No. 3,938,527 discloses a bipolar laparoscopic instrument for tubal cauterization. U.S. Pat. No. 5,250,047 discloses a bipolar laparoscopic instrument with a replaceable electrode tip assembly. U.S. Pat. No. 5,445,638 discloses a bipolar coagulation and cutting forceps with first and second conductors extending from the distal end. U.S. Pat. No. 5,391,166 discloses a bipolar endoscopic instrument having a detachable working end. U.S. Pat. No. 5,342,359 discloses a bipolar coagulation device.

The present invention solves the problem of providing a large closure force between the jaws of a laparoscopic bipolar electrosurgical instrument, using a compact design that fits through a cannula, without risking structural failure of the instrument yoke.

SUMMARY

The present disclosure relates to a laparoscopic bipolar electrosurgical instrument for sealing tissue and includes a handle having an elongated tube affixed thereto. The tube includes first and second jaw members attached to a distal end thereof which are movable from a first position for approximating tissue to at least one subsequent position for grasping tissue therebetween. Each of the jaw members includes an electrically conductive sealing surface. The handle has a fixed handle and a handle which is movable relative to the fixed handle to effect movement of the jaw members from the first position to the at least one subsequent position for grasping tissue. The jaw members are connected to a source of electrosurgical energy such that the jaw members are capable of conducting bipolar electrosurgical energy through the tissue held therebetween. A stop is included for maintaining a minimum separation distance between opposing sealing surfaces and a ratchet is included for maintaining a closure force in the range of about 3 kg/cm$^2$ to about 16 kg/cm$^2$ between opposing sealing surfaces.

Preferably, the stop maintains a minimum separation distance of at least about 0.03 millimeters between opposing sealing surfaces. The stop may be disposed on at least one of the electrically conductive sealing surfaces, or alternatively, the stop may be located adjacent one of the electrically conductive sealing surfaces.

In one embodiment according to the present disclosure, the first jaw member is connected to the bipolar electrosurgical energy source by a pushrod and the second jaw member is connected to the bipolar electrosurgical source by a conductive tube.

In another embodiment, the ratchet is disposed within the fixed handle and at least one complimentary interlocking mechanical interface is disposed on the movable handle. Preferably, the ratchet and the complimentary interlocking mechanical interface provide at least one interlocking position for maintaining a closure force within the range of about 7 kg/cm² to about 13 kg/cm² between opposing sealing surfaces. Ideally, the closure force is in the range of about 4 kg/cm² to about 6.5 kg/cm².

In yet another embodiment according the present disclosure, the laparoscopic bipolar electrosurgical instrument includes a handle having an elongated tube affixed thereto with first and second jaw members attached to a distal end thereof which each include electrically conductive sealing surfaces. The jaw members are movable from a first position for approximating tissue to at least one subsequent position for grasping tissue therebetween. The handle has a fixed handle and a handle which is movable relative to the fixed handle to effect movement of the jaw members from the first position to the at least one subsequent position for grasping tissue. The sealing surfaces include a non-stick material for reducing tissue adhesion during the sealing process. The first and second jaw members are coupled to a source of bipolar electrosurgical energy and a stop is disposed on at least one of the electrically conductive sealing surfaces to maintain a minimum separation distance between the opposable seal surfaces during sealing. A ratchet is disposed on one of the fixed and movable handles and at least one complimentary interlocking mechanical interface is disposed on the other of the fixed and movable handles. Preferably, the ratchet and the complimentary interlocking mechanical interface include at least one interlocking position which maintains a closure force in the range of about 7 kg/cm² to about 13 kg/cm² between opposable seal surfaces.

In one embodiment, the non-stick material is a coating which is deposited on the opposable sealing surfaces. The non-stick coating may be selected from a group of materials consisting of: nitrides and nickel/chrome alloys. Preferably, the non-stick coating includes one of: TiN; ZrN; TiAlN; CrN; nickel/chrome alloys with a Ni/Cr ratio of approximately 5:1; Inconel 600; Ni200; and Ni201.

In one embodiment according to the present disclosure, the opposable sealing surfaces are manufactured from a non-stick material which is a nickel/chrome alloy. For example, the non-stick material may include nickel/chrome alloys with a Ni/Cr ratio of approximately 5:1, Inconel 600, Ni200 and Ni201.

Preferably, at least one of the jaw members, handles and elongated tube includes an insulative material disposed thereon which may be an insulative coating or an insulative sheath.

DETAILED DESCRIPTION

Figure 1:
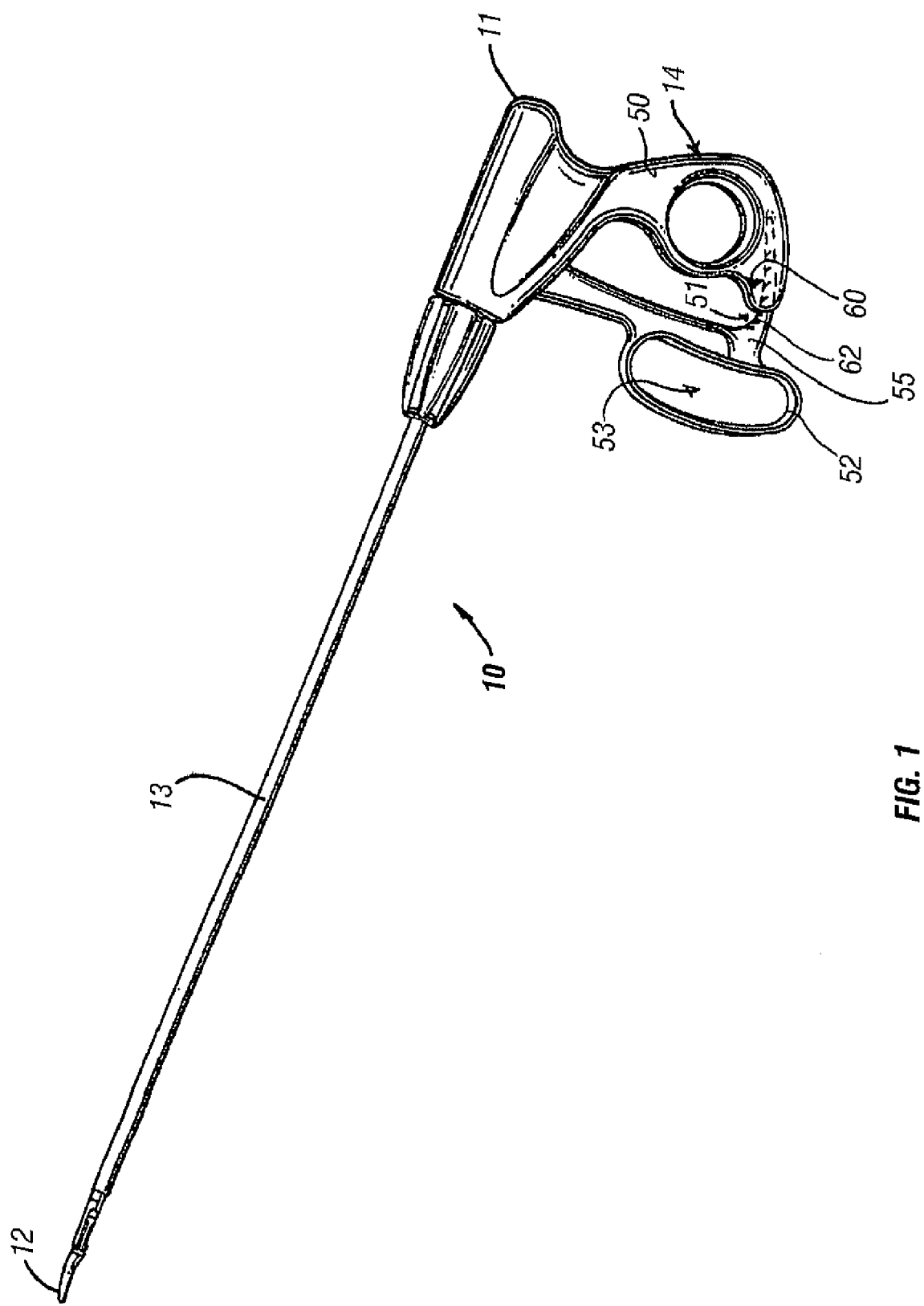
FIG. 1 is a perspective view of a laparoscopic bipolar electrosurgical instrument according to the present disclosure.

A laparoscopic bipolar electrosurgical instrument 10 is shown in FIG. 1. The instrument 10 has a proximal end 11 with a handle 14 for holding and manipulating the instrument 10. A distal end 12 on the instrument 10 is used for surgical manipulation of tissue. The instrument 10 comprises an elongate tube 13 that is sized to fit through a cannula for laparoscopic operations, and in different embodiments may be sized to fit through a five to ten millimeter cannulas.

Figure 2:
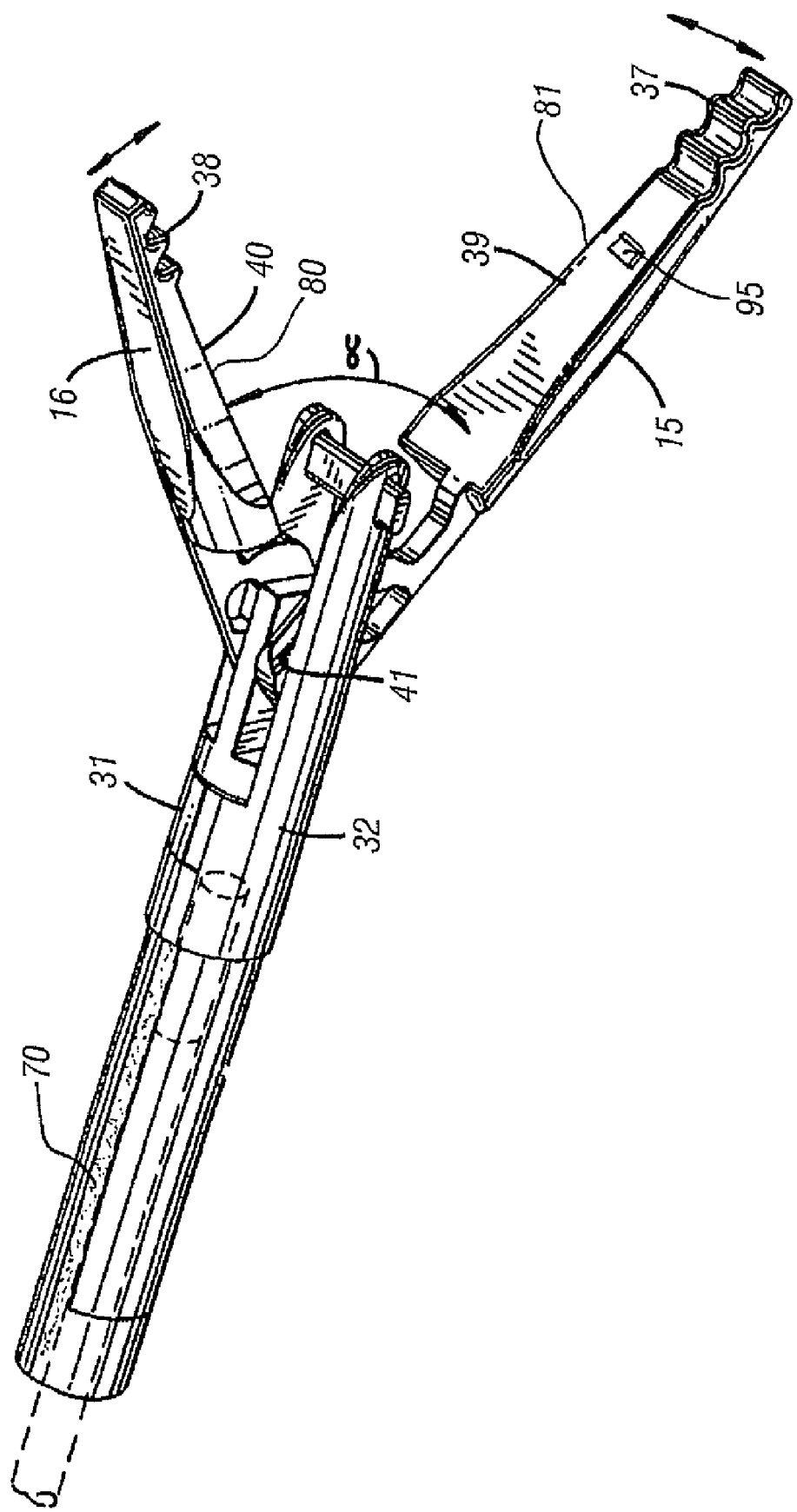
FIG. 2 is a perspective view of the distal end and jaws of the instrument in FIG. 1.

A portion of the distal end 12 of the instrument 10 is shown in FIG. 2. A first jaw 15 and a second jaw 16 are shown in an open position. An angle α is subtended by the jaws 15 and 16. Closing of the jaws 15 and 16 is defined as a reduction of the angle α subtended by the jaws 15 and 16. Similarly, opening of the jaw 15 and 16 is defined as an enlargement of the angle α. The angle α is zero when the jaws 15 and 16 are closed together. The center of rotation for the first jaws 15 is at the first pivot 41, and the center of rotation for the second jaw 16 is at the second pivot 42. The first pivot 41 is located on an outer nose piece 32, and fits in a first pivot hole 43 located on the first flange 18. The second pivot 42 is located on an inner nose piece 31, and fits in a second pivot hole 44 located on the second flange 20.

Figure 3:
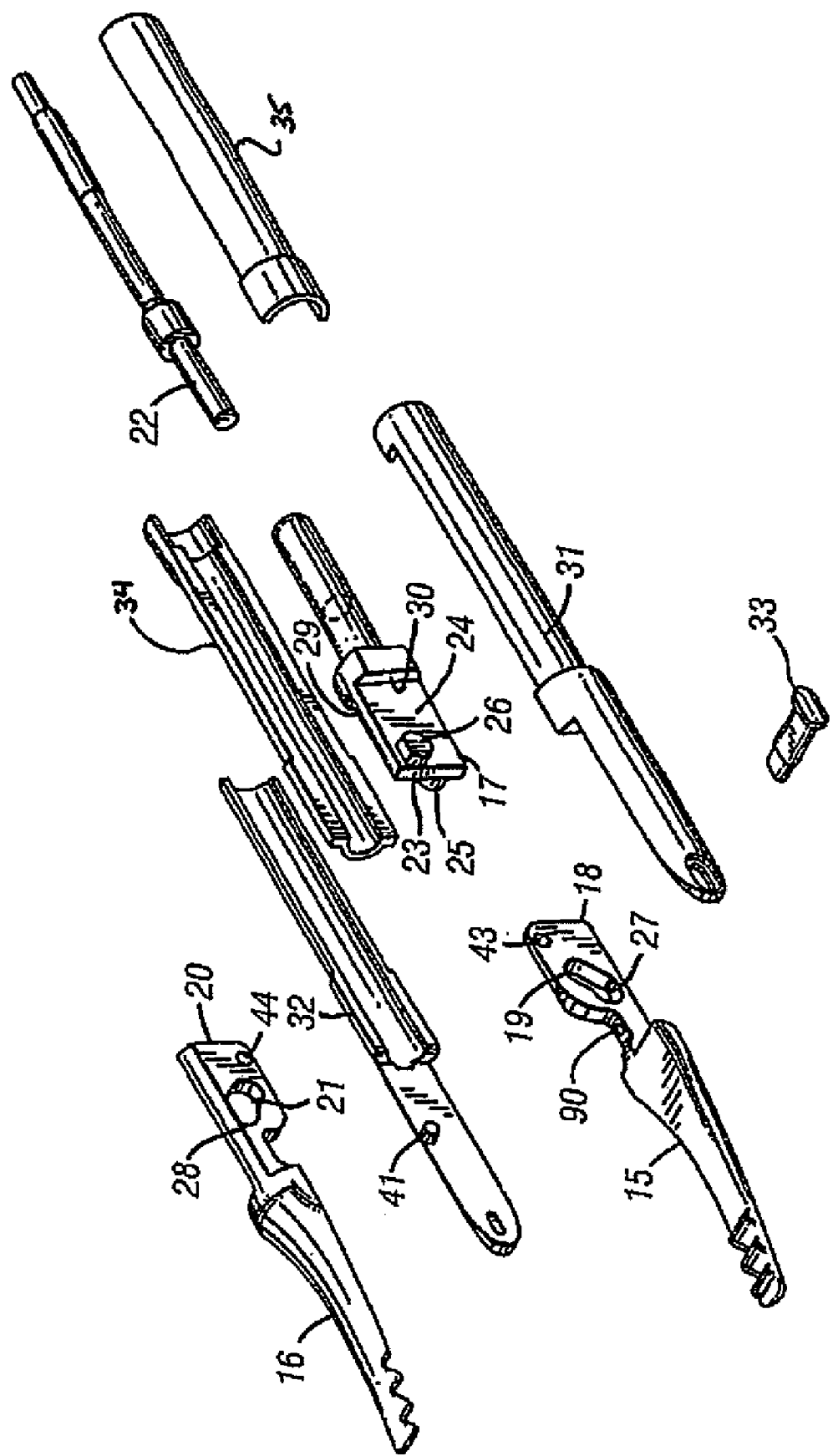
FIG. 3 is an exploded view of the distal end shown in FIG. 2.

Pieces that comprise the distal end 12 of the instrument 10 are shown in an exploded view in FIG. 3. The first jaw 15 and the second jaw 16 are shown separated from a yoke 17. The first jaw 15 has a first flange 18 and a first slot 19 therewithin. The second jaw 16 has a second flange 20 and a second slot 21 therewithin. Each jaw 15 and 16 is preferably formed from a single piece of stainless steel or other electrically conductive material.

Referring again to FIG. 3, the yoke 17 is attached to a pushrod 22. The yoke 17 is preferably formed from an electrically insulative material such as plastic. A first side 23 of the yoke 17 faces the first flange 18. A second side 24 of the yoke 17 faces the second flange 20. When the yoke 17 is positioned between the flanges 18 and 20, the yoke 17 also acts to electrically insulate the first jaw 15 from the second jaw 16. In this manner, bipolar electrosurgical current can be conducted through tissue grasped by the jaws 15 and 16 without short circuiting between the flanges 18 and 20.

A first pin 25 is located on the first side 23 which movably engages the first slot 19. Similarly, a second pin 26 is located on the second side 24 to movably engage the second slot 21. Each pin and slot combination works as a cam-follower mechanical linkage. Motion of the pushrod 22 moves the yoke 17 causing pins 25 and 26 to slide within their respective slots 19 and 21. The slots 19 and 21 are angled with respect to the distal ends of the jaws 15 and 16 such that the jaws 15 and 16 move in an arcuate fashion toward and away from each other. The pins 25 and 26 are different from the pivots 41 and 42. The pins 25 and 26 provide a force against the walls of the slots 19 and 21, creating a moment about the pivots 41 and 42.

The slots 19 and 21 are arranged such that distal motion of the pushrod 22 causes the jaws 15 and 16 to move together. Distal motion of the pushrod 22 is defined as motion in the direction of the distal end 12 of the instrument 10. Once the jaws 15 and 16 are closed together, the present invention holds the jaws 15 and 16 together with a compressive force on the pushrod 22.

One of the advantages of this invention is that shear forces on the pins 25 and 26 can be offloaded to prevent mechanical failure when large forces are being transmitted to the jaws 15 and 16. Each slot 19 and 20 has a cul-de-sac 27 and 28, respectively, as shown in FIG. 3. The first cul-de-sac 27 is an enlargement of the first slot 19 near its distal end. The second cul-de-sac 28 is an enlargement of the second slot 21 near its distal end. The cam-follower motion of the pins 25 and 26 in the slots 19 and 21 will bring the pins 25 and 26 into their respective cul-de-sac 27 and 28. This position of the pins 25 and 26 leaves a very small moment arm between the pins 25 and 26 and the pivots 41 and 42. The yoke 17 has shoulders 29 and 30 that can provide a relatively large moment about the pivots 41 and 42 to effect a high closure force between the jaws 15 and 16 without a high shear forces on the pins 25 and 26, as described below.

Once the pins 25 and 26 are in the cul-de-sacs 27 and 28, the force from the yoke is transmitted to the flanges 18 and 20 by a first shoulder 29 and a second shoulder 30. The shoulders 29 and 30 abut the proximal end of the flanges 18 and 20 to cause the jaws 15 and 16 to close together. The pivots 41 and 42 are preferably made of metal and can withstand relatively high shear forces. In contrast, pins 25 and 26 are preferably made of plastic and will break under relatively high shear forces. Thus, the shoulders 29 and 30 provide a moment about the pivots 41 and 42, thereby avoiding the necessity of applying high shear forces to the pins 25 and 26 wherein the moment arm from the pins 25 and 26 would be small. There is an angle α at which the pins 25 and 26 enter their respective cul-de-sacs 27 and 28 and the shoulders 29 and 30 abut the flanges 18 and 20. The angle α at which the forgoing occurs is preferably around three degrees.

The bipolar electrosurgical instrument 10 has first and second poles of alternating potential that are conducted along the instrument 10 and through tissue that is grasped between the jaws 15 and 16. The first pole is conducted from the proximal end 11 toward the distal end 12 along the pushrod 22. The second pole is conducted from the proximal end 11 toward the distal end 12 along the tube 13. The outer surface of the tube 13 is preferably coated with an electrically insulative material. There is also preferably an electrically insulative barrier between the pushrod 22 and the tube 13 to prevent short circuits in the instrument 10.

In the preferred embodiment, the distal end of the instrument 10 comprises an inner nose piece 31 and an outer nose piece 32, as shown in FIG. 2. The inner nose piece 31 is electrically connected with the pushrod 22, while the outer nose piece is electrically connected with the tube 13. The inner nose piece 31 and the outer nose piece 32 capture the yoke 17, along with the first and second flanges 18 and 20, as shown in FIG. 2. The yoke 17 moves axially, along an axis defined by the tube 13, in a space between the inner and outer nose pieces 31 and 32. A spacer stake 33 maintains the separation of the nose pieces 31 and 32 at their distal ends. The nose pieces 31 and 32 provide lateral support for the flanges 18 and 20 to help ensure that the pins 25 and 26 remain within the slots 19 and 21, respectively.

Figure 4:
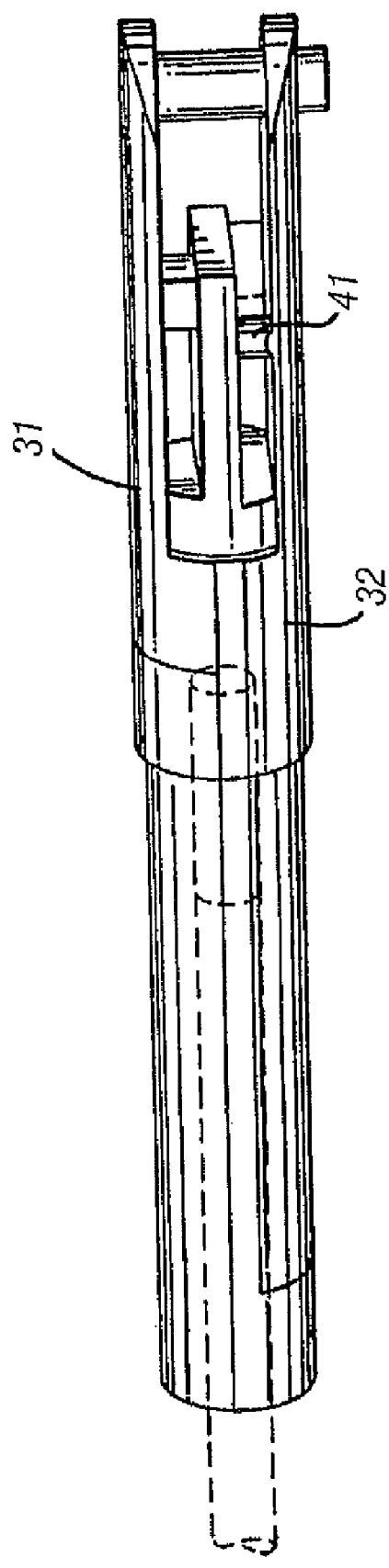
FIG. 4 is perspective view of the distal end of the instrument with the jaws removed.
Figure 5:
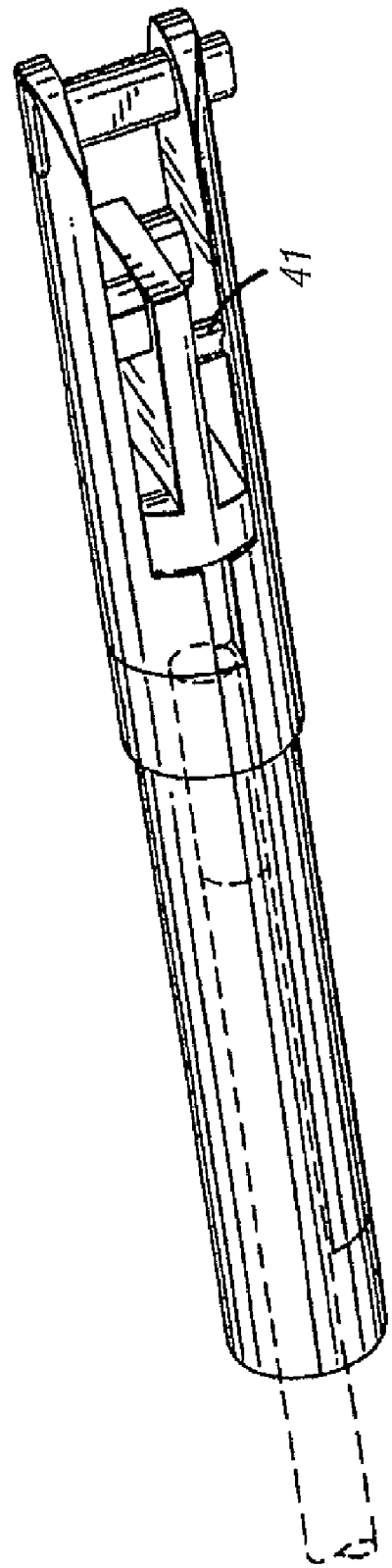
FIG. 5 is another perspective of FIG. 4.
Figure 6:
FIG. 6 is a side view of an electrical spring contact.
Figure 7:
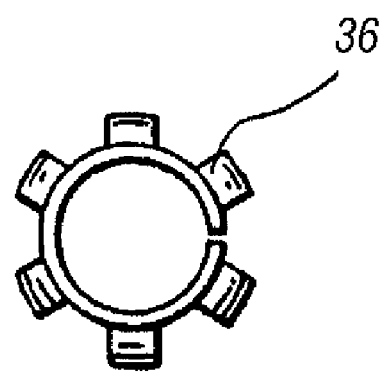
FIG. 7 is a front view of the spring contact shown in FIG. 6.

The preferred embodiment also comprises an inner insulator 34 and an outer insulator 35 for maintaining electrical insulation between the poles. The outer insulator 35 is seated between the tube 13 and the inner nose 31, as shown in FIGS. 2 and 4. The inner insulator 34 is seated between the tube 13 and the pushrod 22. In this manner, the outer nose piece 32 can provide electrical continuity between the tube 13 and the second jaw 16, while the inner nose piece 34 can provide electrical continuity between the pushrod 22 and the first jaw 15. Since the pushrod 22 is slidably mounted within the tube 13, the preferred embodiment has a spring contact 36, as shown in FIGS. 6 and 7, which is mounted on the pushrod 22 to maintain an electrical connection with the inner nose piece 34 during axial motion.

The first and second jaws 15 and 16 each have ridges 37 and 38 at their distal ends that preferably nest together. The jaws 15 and 16 also have seal surfaces 39 and 40, as shown in FIG. 2. The width of the seal surfaces 39 and 40 is a parameter that affects the quality of the surgical outcome. The closure force between the jaws 15 and 16 varies along the length of the seal surfaces 39 and 40, with the largest force at the distal tip and the smallest force at the proximal end of the seal surfaces 39 and 40. It is known that the amount of pressure exerted on the tissue depends on the surface area of the tissue that is in contact with the seal surfaces. In the one embodiment, the width of each seal surface, e.g., 39, is in the range of about 2 to about 5 millimeters, and preferably 4 millimeters width, while the length of each seal surface 39 and 40 is preferably in the range of about 10 to 30 millimeters.

It has been found through experimentation that good vessel sealing results are obtained when the closure force in grams divided by the width in millimeters is in the range of about 400 to 650 grams per millimeter of seal surface width. Since the closure force varies with the length of the seal surfaces 39 and 40, it has been found to be advantageous to taper the width of the seal surfaces 39 and 40 along their length, with the widest width at the proximal end and the narrowest width at the distal end. For example, if the width of the seal surface 39, 40 is 4 millimeters, the closure force is preferably in the range of about 1600 grams to about 2600 grams This design allows the jaws 15 and 16 to apply a relatively constant closure force per unit width, preferably 525 grams per millimeter width which yields a closure force of 2100 grams for a 4 millimeter width seal surface 39, 40.

In one embodiment, the handle 14 includes a fixed handle 50 having a channel 51 defined therein which slidingly receives a movable handle 52. Movable handle 52 includes a handgrip 53 defined therein which allows a user to move handle 52 relative to fixed handle 50. Movable handle 52 also includes a flange 55 having a series of grooves 62 defined therein which mechanically inter-engage a corresponding ratchet 60 disposed within channel 51. Preferably, the ratchet 60 and groove 62 are dimensioned such that successive ratchet positions will yield pressures within a predetermined working range of about 7 kg/cm$^2$ to about 13 kg/cm$^2$. In one embodiment, the successive ratchet positions are two millimeters apart.

Experimental results in tissue studies suggest that the magnitude of pressure exerted on the tissue by the seal surfaces 39 and 40 is important in assuring a proper surgical outcome. Tissue pressures within a working range of about 3 kg/cm$^2$ to about 16 kg/cm$^2$ and, preferably, within a working range of 7 kg/cm$^2$ to 13 kg/cm$^2$ have been shown to be effective for sealing arteries and vascular bundles. Tissue pressures within the range of about 4 kg/cm$^2$ to about 6.5 kg/cm$^2$ have proven to be particularly effective in sealing arteries and tissue bundles.

A method of making a laparoscopic bipolar electrosurgical instrument 10 is also herein described. The method comprises the step of forming a first jaw 15 having a first flange 18 with a first slot 19, and a second jaw 16 having a second flange 20 with a second slot 21. The jaws 15 and 16 are preferably formed in a casting process, although it is also possible to machine the jaws 15 and 16 from stock. The casting process may include injecting powdered metal under pressure into a mold, and then applying heat.

Other steps in the method include attaching a yoke 17 to a pushrod 22, and electrically insulating the first flange 18 from the second flange 20 with the yoke 17. The yoke 17 is preferably an injection molded plastic part with features including a first shoulder 29 and a second shoulder 30.

During assembly of the distal portion of the instrument 10, steps in the method include engaging a first pin 25 with the first slot 19, and engaging a second pin 26 with the second slot 21. The slots 19 and 21 are shaped such that a subtended angle α between the first and second jaws 15 and 16 decreases with distal motion of the pushrod 17. The slots 19 and 20 are formed with cul-de-sacs 27 and 28 positioned to relieve shear stresses on the first and second pins 25 and 26 at the subtended angle α approximately where the first and second shoulders 29 and 30 engage the first and second flanges 18 and 20.

Further steps in the method comprise: surrounding at least a portion of the pushrod 22 with an electrically conductive tube 13; electrically insulating the tube 13 from the pushrod 22; electrically connecting an inner nose piece 31 to the pushrod 22, and electrically connecting an outer nose piece 32 to the tube 13, wherein the inner nose piece 31 and the outer nose piece 32 capture the yoke 17 along with the first and second flanges 18 and 20 to conduct bipolar electrosurgical current to the first and second jaws 15 and 16. In the preferred embodiment, there is a step of electrically connecting the pushrod 22 and the inner nose piece 31 with a spring contact 36.

The method of making the instrument 10, in some embodiments, includes the steps of tapering the width of the seal surfaces 39 and 40 along the length of each of the first and second jaws 15 and 16.

An electrically insulative coating 70 may be included to substantially cover the elongated tube 13 to protect the surgeon against electrical arcs. Other parts of the instrument may also be protected by the insulative coating 70. An insulative sheath may also be used to cover tube 13 or other components of the instrument 10, e.g., the proximal end 11, handles 50, 52 and the outer surfaces (non-opposing surfaces) of the jaw members 15, 16.

It is envisioned that the outer surface of the jaw members 15 and 16 may include a nickel-based material, coating, stamping, metal injection molding which is designed to reduce adhesion between the jaw members (or components thereof) with the surrounding tissue during activation and sealing. Moreover, it is also contemplated that other components such as the tube 13 and handles 50, 52 may also be coated with the same or a different "non-stick" material. Preferably, the non-stick materials are of a class of materials that provide a smooth surface to prevent mechanical tooth adhesions.

It is also contemplated that the tissue sealing surfaces 39 and 40 of the jaw members 15 and 16, respectively, may be manufactured from one (or a combination of one or more) of the following "non-stick" materials: nickel-chrome, chromium nitride, MedCoat 2000 manufactured by The Electrolizing Corporation of OHIO, Inconel 600 and tin-nickel. For example, high nickel chrome alloys and Ni200, Ni201 (.about.100% Ni) may be made into electrodes or sealing surfaces by metal injection molding, stamping, machining or any like process.

In addition these materials preferably include an optimal surface energy for eliminating sticking due in part to surface texture and susceptibility to surface breakdown due electrical effects and corrosion in the presence of biologic tissues. It is envisioned that these materials exhibit superior non-stick qualities over stainless steel and should be utilized on the instrument in areas where the exposure to pressure and RF energy can create localized "hot spots" more susceptible to tissue adhesion. As can be appreciated, reducing the amount that the tissue "sticks" during sealing improves the overall efficacy of the instrument.

The tissue sealing surfaces 39 and 40 may also be "coated" with one or more of the above materials to achieve the same result, i.e., a "non-stick surface". For example, Nitride coatings (or one or more of the other above-identified materials) may be deposited as a coating on another base material (metal or nonmetal) using a vapor deposition manufacturing technique.

One particular class of materials disclosed herein has demonstrated superior non-stick properties and, in some instances, superior seal quality. For example, nitride coatings which include, but are not limited to: TiN, ZrN, TiAlN, and CrN are preferred materials used for non-stick purposes. CrN has been found to be particularly useful for non-stick purposes due to its overall surface properties and performance. Other classes of materials have also been found to reducing overall sticking. For example, high nickel/chrome alloys with a Ni/Cr ratio of approximately 5:1 have been found to significantly reduce sticking in bipolar instrumentation. One particularly useful non-stick material in this class is Inconel 600. Bipolar instrumentation having electrodes made from or coated with Ni200, Ni201 (.about.100% Ni) also showed improved non-stick performance over typical bipolar stainless steel electrodes.

It has been found experimentally that local current concentrations can result in an uneven tissue effect, and to reduce the possibility of this outcome, each seal surface 39 and 40 may include a radiused edge 80, 81. As mentioned above, a tapered seal surface 39 and 40 has been shown to be advantageous in certain embodiments because the taper allows for a relatively constant pressure on the tissue along the length of the seal surfaces 39 and 40. The width of the seal surfaces 39 and 40 may be adjusted to assure that the closure force divided by the width is approximately constant along the length.

In one embodiment, a stop 90, made from insulative material, is located in the instrument to maintain a minimum separation of at least about 0.03 millimeters between the seal surfaces 39 and 40, as shown in FIG. 3. Preferably, the stop maintains a minimum separation distance in the range of about 0.03 millimeters to about 0.16 millimeters. The stop 90 reduces the possibility of short circuits between the seal surfaces 39 and 40. It is envisioned that stop 90 may be positioned proximate the pivots 41 and 42, proximate the stake 33 or adjacent the opposable seal surfaces 39 and 40.

In another embodiment, the instrument 10 includes a second or alternative stop 95 which is designed to maintain a minimum separation of at least about 0.03 millimeters between the seal surfaces 39 and 40, as shown in FIG. 2. Preferably, the stop 90 and/or the stop 95 maintains a separation distance within the range of about 0.03 millimeters to about 0.16 millimeters. A plurality of stops 90 and/or 95 (or various patterns of stops 90, 95) may also be utilized to accomplish this purpose.

It is to be understood that the above described embodiments are only illustrative of the application of the principles of the present invention. Numerous modifications and alternative arrangements may be devised by those skilled in the art without departing from the spirit and scope of the present invention. The appended claims are intended to cover such modifications and arrangements.

What is claimed is:

1. A laparoscopic bipolar electrosurgical instrument, comprising:

a handle selectively movable to actuate a pair of first and second opposable jaw members attached to a distal end thereof, the jaw members movable from a first position for approximating tissue to at least one subsequent position for grasping tissue therebetween, each of the jaw members including an electrically conductive sealing surface and adapted to connect to a source of electrosurgical energy such that the sealing surfaces are capable of conducting electrosurgical energy through tissue held therebetween;

an electrically conductive pushrod for connecting the first jaw member to the source of electrosurgical energy;

an electrically conductive tube for connecting the second jaw member to the source of electrosurgical energy;

an electrically insulative yoke coupled to the pushrod and dimensioned to operatively engage each of the jaw members to affect movement thereof;

an inner nose piece electrically connected between the first jaw member and the electrically conductive pushrod;

an outer nose piece electrically connected between the second jaw member and the electrically conductive tube; wherein the inner nose piece and the outer nose piece capture the yoke;

an inner insulator disposed between the electrically conductive tube and the electrically conductive pushrod; and an outer insulator disposed between the electrically conductive tube and the inner nose piece.

2. A laparoscopic bipolar electrosurgical instrument of claim 1, further comprising an electrical spring contact operably disposed between the electrically conductive pushrod and the inner nose piece to provide electrical continuity therebetween.

3. A laparoscopic bipolar electrosurgical instrument according to claim 1, further comprising a stop for maintaining a minimum separation distance of at least about 0.03 millimeters between the sealing surfaces.

4. A laparoscopic bipolar electrosurgical instrument according to claim 3, wherein the stop is disposed on at least one of the sealing surfaces.

5. A laparoscopic bipolar electrosurgical instrument according to claim 3, wherein the stop maintains a minimum separation distance between the sealing surfaces in the range of about 0.03 millimeters to about 0.16 millimeters.

6. A laparoscopic bipolar electrosurgical instrument according to claim 3, further comprising a ratchet selectively positionable to maintain a closure force in the range of about 3 $kg/cm^2$ to about 16 $kg/cm^2$ between the sealing surfaces.

7. A laparoscopic bipolar electrosurgical instrument according to claim 1, further comprising a ratchet selectively positionable to maintain a closure force in the range of about 3 $kg/cm^2$ to about 16 $kg/cm^2$ between the sealing surfaces.

* * * * *